United States Patent [19]

Young et al.

[11] Patent Number: 5,281,720
[45] Date of Patent: Jan. 25, 1994

[54] PYRANYLPHENYL HYDROXYALKYLNAPHTHOIC ACIDS AS INHIBITORS OF LEUKOTRIENE BIOSYNTHESIS

[75] Inventors: Robert N. Young, Senneville; Yves Girard, Ile Bizard; John W. Gillard, Baie d'Urfe; Laird A. Trimble; John Scheigetz, both of Dollard des Ormeaux; James A. Yergey, St. Lazare; Yves Ducharme, Montreal; Deborah A. Nicoll-Griffith, Baie d'Urfe; John H. Hutchinson, Montreal, all of Canada

[73] Assignee: Merck Frosst Canada, Inc., Kirkland

[21] Appl. No.: 966,204

[22] Filed: Oct. 26, 1992

Related U.S. Application Data

[63] Continuation of Ser. No. 834,912, Feb. 13, 1992, abandoned, which is a continuation-in-part of Ser. No. 662,535, Feb. 28, 1991, abandoned.

[51] Int. Cl.$^5$ ............... A61K 31/35; C07D 309/30; C07D 309/06; C07D 311/94
[52] U.S. Cl. ............... 549/13; 549/28; 549/417; 549/426; 549/427; 549/428; 546/205; 546/206; 546/239; 544/239; 544/172
[58] Field of Search ............ 549/13, 28, 417, 426, 549/427, 428; 546/239, 205, 206; 544/239, 172

[56] References Cited

U.S. PATENT DOCUMENTS

| | | | |
|---|---|---|---|
| 4,486,445 | 12/1984 | Patel et al. | 549/299 |
| 4,937,373 | 6/1990 | Carson | 560/56 |

FOREIGN PATENT DOCUMENTS

| | | | |
|---|---|---|---|
| 0381375 | 8/1980 | European Pat. Off. | 560/50 |
| 0188248 | 7/1986 | European Pat. Off. | 560/56 |
| 0351194 | 1/1990 | European Pat. Off. | 560/56 |
| 0372385 | 6/1990 | European Pat. Off. | 560/56 |
| 0375368 | 6/1990 | European Pat. Off. | 560/56 |
| 0375404 | 6/1990 | European Pat. Off. | 560/56 |
| 0375452 | 6/1990 | European Pat. Off. | 560/56 |
| 0380982 | 8/1990 | European Pat. Off. | 560/56 |
| 0385662 | 9/1990 | European Pat. Off. | 560/56 |
| 0385663 | 9/1990 | European Pat. Off. | 560/56 |
| 0385679 | 9/1990 | European Pat. Off. | 560/56 |
| 0385680 | 9/1990 | European Pat. Off. | 560/50 |
| 0409413 | 1/1991 | European Pat. Off. | 560/56 |
| 0462812 | 12/1991 | European Pat. Off. | 549/13 |
| 0462830 | 12/1991 | European Pat. Off. | 549/13 |

*Primary Examiner*—Robert T. Bond
*Attorney, Agent, or Firm*—Mark R. Daniel; Joseph F. DiPrima

[57] ABSTRACT

Compounds having the formula I:

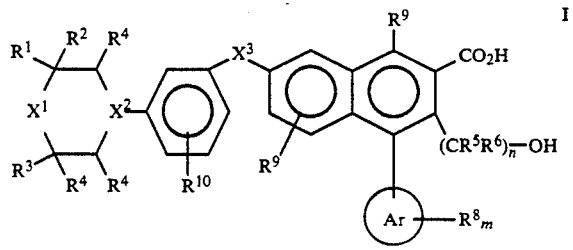

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

4 Claims, No Drawings

PYRANYLPHENYL HYDROXYALKYLNAPHTHOIC ACIDS AS INHIBITORS OF LEUKOTRIENE BIOSYNTHESIS

CROSS-REFERENCE

This is a continuation of application Ser. No. 07/834,912 filed Feb. 13, 1992, abandoned, which ia a CIP of U.S. Ser. No. 662,535, Feb. 28, 1991, abandoned.

BACKGROUND OF THE INVENTION

The leukotrienes constitute a group of locally acting hormones, produced in living systems from arachidonic acid. The major leukotrienes are Leukotriene $B_4$ (abbreviated at $LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxyzenases*, ed. J. Rokach, Elsevier, Amsterdam (1989). The actions of the leukotrienes in living systems and their contribution to various diseases states are also discussed in the book by Rokach.

EP 375,404 (27 June 1990) describes certain naphthalene-containing heterocyclic ethers of structure A which are inhibitors of the enzyme 5-lipoxygenase. EP 375,452 (27 June 1990) describes naphthalene-containing hydrocarbon ethers of structure B which are reported to possess the same activity. Both of these series of compounds differ significantly from the present invention in that they lack the major aryl substituent.

$$Ar^1-A^1-O-Ar^2-\overset{OR^1}{\underset{R^3}{C}}-R^2 \qquad A$$

EP 375,404 ICI-Pharma $$Ar^1-A^1-O-Ar^2-\overset{OR^1}{\underset{R^3}{C}}-R^2 \qquad B$$

EP 375,452 ICI-Pharma

SUMMARY OF THE INVENTION

The present invention relates to pyranylphenyl hydroxyalkylnaphthoic acids having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

DETAILED DESCRIPTION OF THE INVENTION

The compounds of the-present invention may be represented by the following formula I:

wherein:

$R^1$ and $R^5$ are independently H, OH, lower alkyl, or lower alkoxy;

$R^2$ is H, lower alkyl or together with $R^1$ forms a double bonded oxygen (=O);

$R^3$ is H, lower alkyl or together with $R^1$ forms a carbon bridge of 2 or 3 carbon atoms, said bridge optionally containing a double bond;

each $R^4$, $R^6$ and $R^7$ is independently H or lower alkyl;

$R^8$ is halogen, lower alkyl, or lower alkoxy;

each $R^9$ is independently H, halogen, lower alkyl, or lower alkoxy;

$R^{10}$ is H, halogen, lower alkyl, or lower alkoxy;

$X^1$ is O, S, S(O)o S(0)$_2$, or CH$_2$;

$X^2$ is N, N(O), C(OR$^7$), or C(R$^7$);

$X^3$ is CH$_2$O, OCH$_2$, or CH$_2$CH$_2$;

Ar is phenyl or 1- or 2-naphthyl;

m is 0, 1, or 2;

n is 1 or 2;

or the pharmaceutically acceptable salts thereof.

It will be obvious to one skilled in the art that if $R^5$ is OH or lower alkoxy on the same carbon atom as the OH group of I, the elements of water or an alcohol may be lost to give an aldehyde or ketone.

Definitions

The following abbreviations have the indicated meanings:

Ac = acetyl
Bn = benzyl
i-Pr = isopropyl
n-Pr = normal propyl
n-Bu = normal butyl
i-Bu = isobutyl
s-Bu = secondary butyl
t-Bu = tertiary butyl
Et = ethyl
Me = methyl
Ph = phenyl
RIA = radio immuno assay
TFAA = trifluoroacetic anhydride
AIBN = azoisobutyronitrile
LDA = lithium diisopropylamide
DMSO = dimethylsulfoxide
Ts = p-toluenesulfonate = tosylate
Ms = methanesulfonate = mesylate
Et$_3$N = triethylamine
DMF = N,N-dimethylformamide
Tf = trifluoromethanesulfonyl
DHP = dihydropyran
DIPHOS = 1,2-bis(diphenylphosphino)ethane
DMAP = 4-dimethylaminopyridine
NBS = N-bromosuccinimide
THP = tetrahydropyran
PCC = pyridinium chlorochromate Alkyl is intended to include linear and branched structures and combinations thereof.

"Alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Lower alkoxyl" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

Halogen means F, Cl, Br, and I.

it is intended that the definitions of any substituent (e.g., $R^4$, $R^7$, etc.) in a particular molecule be independent of its definitions elsewhere in the molecule. Thus, $-(CR^5R^6)_2-$ represents $CH_2CH_2$, $CH(CH_3)CH_2$, $C(CH_3)2CH(CH_3)$, etc.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, t.heobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) multiple sclerosis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gas-Uric damage; trauma- or stress-induced cell damage; and glycerol-induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of Formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic o.r heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

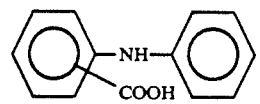

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

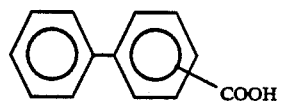

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

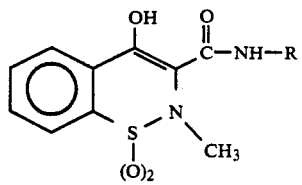

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, flupro-quazone, fopirtoline, fosfosal, furcloprofen, glucametacin, gualmesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDS, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR$^{714}$, MR$^{897}$, MY309, ON03144, PR$^{823}$, PV102, PV108, R$^{830}$, RS2131, SCR$^{152}$, SH440, SIR$^{133}$, SPAS510, SQ27239, ST281, SY6001, TA60, TAI-901 (4-benzoyl-1-indancarboxylic acid), TVX2706, U60257, UR$^{2301}$, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. 4,237,160. They may also contain histidine decarboxylase inhibitors such as α-fluoromethyl-histidine, described in U.S. Pat. 4,325,961. The compounds of the Formula I may also be advantageously combined with an H$_1$- or H$_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K$^+$/H$^+$ ATPase inhibitor such as omeprazole, disclosed in U.S. Pat. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the formula I of the present invention may be prepared according to the synthetic routes outlined in the Schemes I to VII and by following the methods described herein.

SCHEME I

The lactone intermediate IX of Scheme I may be prepared, in a multistep sequence, from 3-benzyloxy benzaldehyde (II). The aldehyde II is firstly converted to the dibromide product III by treatment with $CBr_4$ and triphenylphosphine in an organic solvent such as $CH_2Cl_2$. Subsequent treatment of III with base such as n-butyllithium in an organic solvent such as THF followed by quenching with $CO_2$ leads to the acid IV. Conversion of IV to the ester V via the acyl chloride is achieved by treatment of IV with oxalyl chloride in an organic solvent such as toluene and DMF followed by addition of a 3-aryl-2-propyn-1-ol and a base such as $Et_3N$ in an organic solvent such as THF. The intramolecular cyclisation of the ester V to provide VI is achieved by heating in an organic acid such as acetic acid. From this reaction, two side-products (VII and VIII) may also be isolated in varying amounts. The debenzylation process is achieved under acidic conditions such as HCl in hot acetic acid leading to the lactone intermediate IX.

SCHEME II

The lactone intermediate IX may also be prepared from a 2-bromo-5-benzyloxy benzaldehyde dimethyl acetal X as outlined in Scheme II. The bromo derivative X is converted to the alcohol XI by treatment with a base such as n-butyl lithium in an organic solvent such as hexane followed by the addition of an aryl carboxaldehyde such as benzaldehyde in an organic solvent such as THF. The Diels-Alder reaction is achieved by heating the alcohol XI in the presence of maleic anhydride in an organic solvent such as toluene, providing the anhydride XII. The reduction of the anhydride XII by treatment with a reducing agent such as $Zn(BH_4)_2$ in an organic solvent such as DMF provides the lactone VI. The debenzylation process to provide the lactone IX is described in Scheme I.

SCHEME III

An alternate route may also be used to prepare the lactone intermediate IX as outlined in Scheme III. The 2-bromo-5-benzyloxybenzaldehyde XIV is firstly converted to the thioacetal XV by treatment with 1,3-propanedithiol in the presence of a Lewis acid such as $BF_3/Et_2O$ in an organic solvent such as $CH_2Cl_2$. The bromothioacetal XV is converted to the alcohol XVI under treatment with a base such as n-butyllithium in an organic solvent such as hexane followed by the addition of an aryl carboxaldehyde such as benzaldehyde in an organic solvent such as THF. Heating the alcohol XVI in the presence of maleic anhydride in an organic solvent such as toluene, provides the Diels-Alder adduct XII. The final conversion of the anhydride XII to the lactone intermediate IX via the benzylated lactone VI is described above.

SCHEME IV

Another route which may be used to provide the lactone intermediate IX is outlined in Scheme IV. The bromoacetal X is firstly converted to the ketoacetal XVII by treatment with a base such as n-butyllithium in an organic solvent such as hexane in the presence of $CuBr/SMe_2$ followed by the addition of an aroyl halide such as benzoyl chloride in an organic solvent such as THF. The ketoacetal XVII is hydrolysed to the ketoaldehyde XVIII by acidic treatment such as HCl in acetone-water. The Diels-Alder reaction is achieved by heating the ketone XVIII in the presence of an N-arylmaleimide such as N-phenylmaleimide and triethylphosphite in an organic solvent such as benzene, providing the imide XIX. The imide XIX is hydrolysed to the dicarboxylic acid XX under basic conditions such as NAOH in water, then after acidification with acid, such as HCl in water, and treatment with trifluoroacetic anhydride, the anhydride XII is isolated. The final conversion of XII to the lactone intermediate IX is described in Scheme II.

SCHEME V

The preparation of compounds of Formula I (wherein $X^3$—$CH_2O$—) is described in Scheme V. Coupling of the phenol lactone IX with the appropriate benzyl halide XXI such as 3-[4-(4-methoxy)tetrahydropyranyl]benzyl bromide in an organic solvent such as DMF using an inorganic base such as $K_2CO_3$ provides the lactone XXII.

SCHEME VI

The synthesis of compounds of Formula I (wherein $X^3$=—$OCH_2$—) is described in Scheme VI. The phenol lactone IX is converted to the triflate XXIII by treatment with trifluoromethanesulfonic anhydride in the presence of an organic base such as pyridine in a solvent such as $CH_2Cl_2$. Subsequent treatment of XXIII in a solvent such as DMSO/methanol with an organic base such as triethylamine, a phosphine such as 1,1'-bis(diphenylphosphino)ferrocene, a palladium(II) salt such as palladium(II)acetate under an atmosphere of carbon monoxide leads to the ester XXIV. The hydrolysis of the ester XXIV is achieved using an inorganic base such as lithium hydroxide in water and the resulting acid XXV is reduced to the alcohol XXVI by treatment with a chloroformate such as isopropyl chloroformate in the presence of an organic base such as triethylamine in an organic solvent such as THF, followed by addition of a reducing agent such as sodium borohydride in water. The alcohol XXVI is then converted to the halide XXVII by treatment with triphenylphosphine, imidazole and $CBr_4$ in an organic solvent such as $CH_2Cl_2$. Coupling of halide XXVII with the appropriate phenol XXVIII such as 3-[4-(4-methoxy)tetrahydropyranyl]phenol in an organic solvent such as DMF using an inorganic base such as $K_2CO_3$ provides the lactone XXIX.

SCHEME VII

Scheme VII illustrates the conversion of lactone XXII (Scheme V) and lactone XXIX (Scheme VI) to lactone XXXI. Lactones XXII and XXIX can be alkylated at the methylene group as shown by treatment with a strong base such as lithium diisopropylamide in an organic solvent such as THF, followed by quenching with an alkyl halide such as methyl iodide. A second alkylation may be achieved by using the same conditions. Conversion of lactones XXII and XXIX to lactone XXXI (wherein $R^5$=OH, $R^6$=H) may be achieved by an hydrolysis process using an inorganic base such as NAOH in a solvent such as $EtOH/H_2O$ to provide the carboxylate salt XXX, followed by an oxidation step using an oxidizing agent such as pyridinium chlorochromate in an organic solvent such as $CH_2Cl_2$.

The hydrolysis of lactones XXII (Scheme V), XXIX (Scheme IV) and XXXI (Scheme VII) using an inorganic base such as NAOH in a solvent such as EtOH/H$_2$O provides compounds of Formula I of the present invention. It will be evident to one skilled in the art that a variety of cationic salt forms of I can be prepared in this way or by cation exchange processess.

Lactone XXXI (R$^5$=OH, R$^6$=H) may be reacted with a lower alkyl Grignard or lithium reagent to prepare XXXI, wherein R$^5$=lower alkyl, R$^6$=H.

SCHEME VIII

Another alternative route which may be used to prepare the lactone IX is outlined in Scheme VIII. The aryl carboxaldehyde XXIX is converted to the thioacetal XXX by treatment with thiophenol in the presence of a Lewis-Acid such as BF$_3$.Et$_2$O in an organic solvent such as isopropyl acetate. The thioacetal XXX is then converted to the lactone XXXII by treatment with a base such as n-butyl lithium in an organic solvent such as THF followed by the successive additions of 2-(5H) furanone and the benzyloxyaryl carboxaldehyde XXXI in an organic solvent such as THF and after quenching with an acid such as HOAC. The cyclization, dehydration and debenzylation are achieved simultaneously by heating the lactone XXXII in the presence of an acid such as trifluoroacetic acid, and using thioanisole as organic solvent providing the lactone IX.

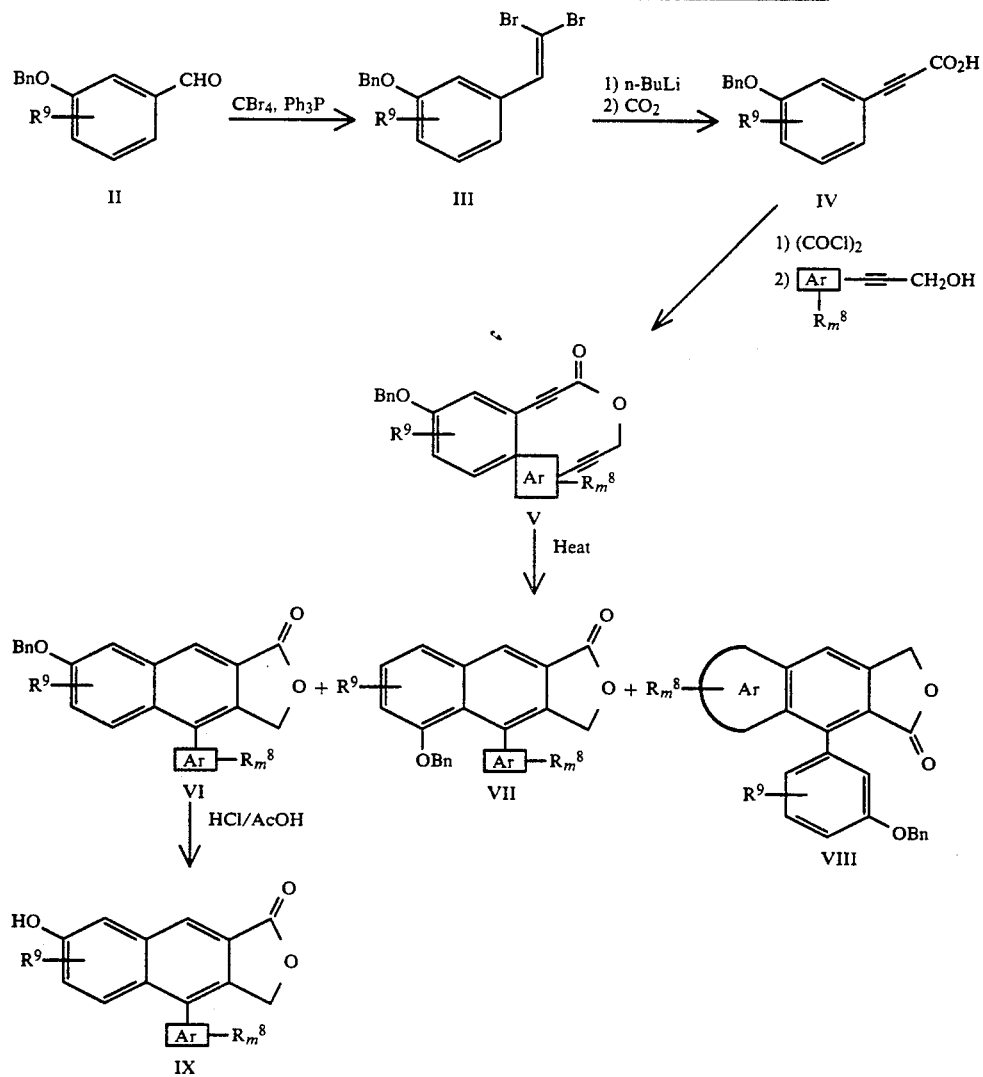

SCHEME I
PREPARATION OF LACTONE INTERMEDIATES (METHOD A)

SCHEME II
PREPARATION OF LACTONE INTERMEDIATES (METHOD B)
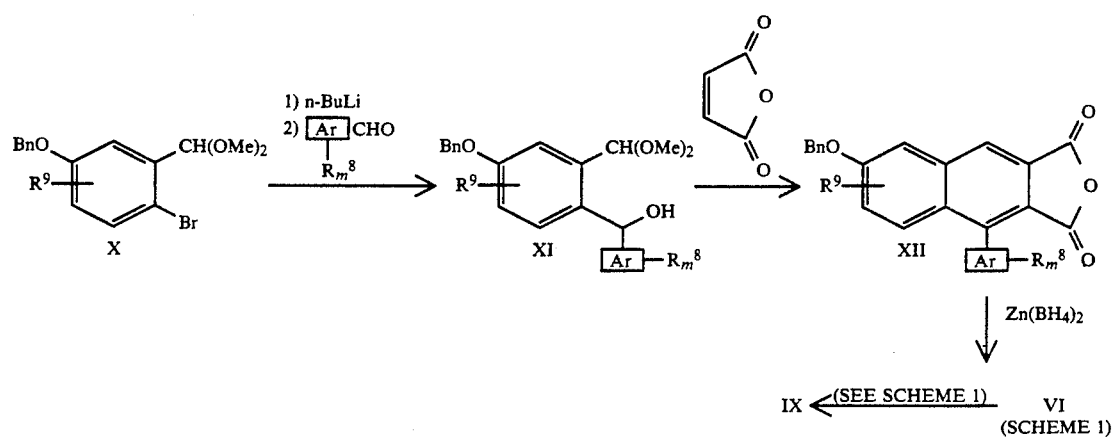
SCHEME III
PREPARATION OF LACTONE INTERMEDIATES (METHOD C)
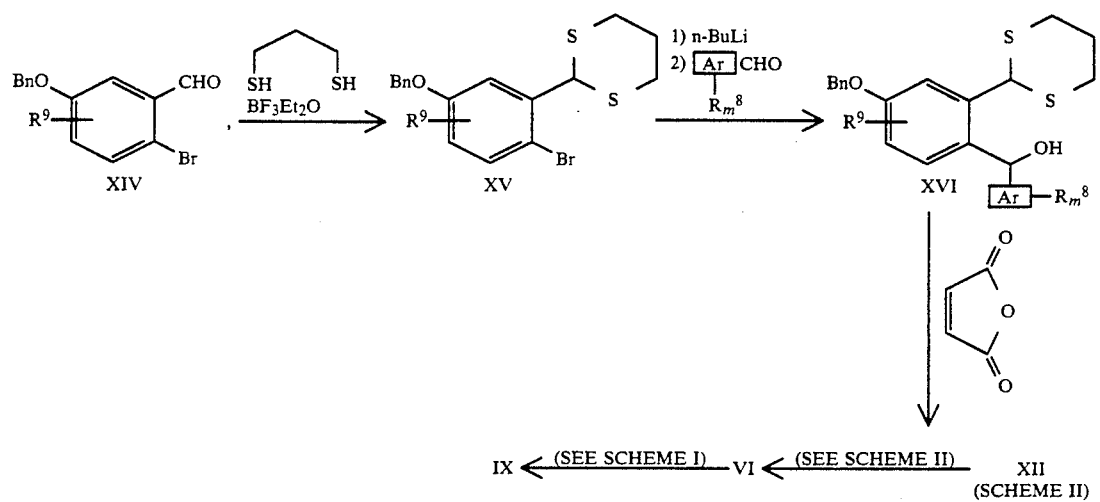
SCHEME IV
PREPARATION OF LACTONE INTERMEDIATES (METHOD D)
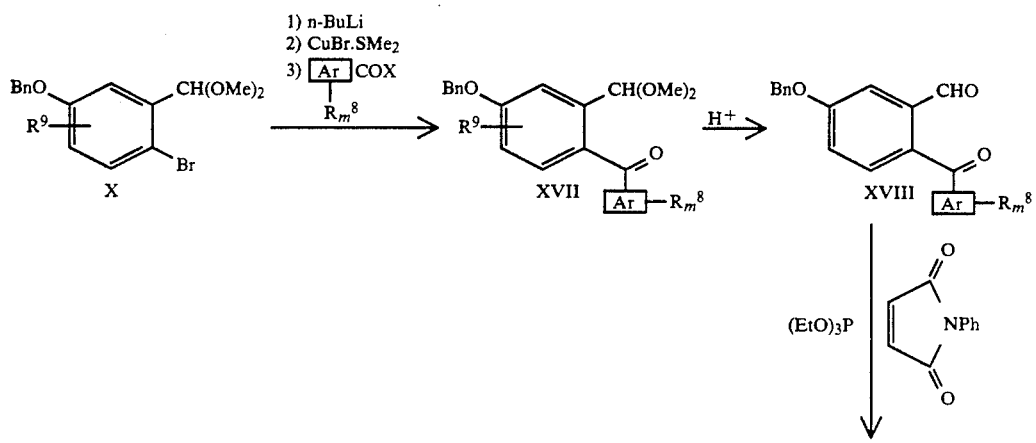

-continued
SCHEME IV
PREPARATION OF LACTONE INTERMEDIATES (METHOD D)
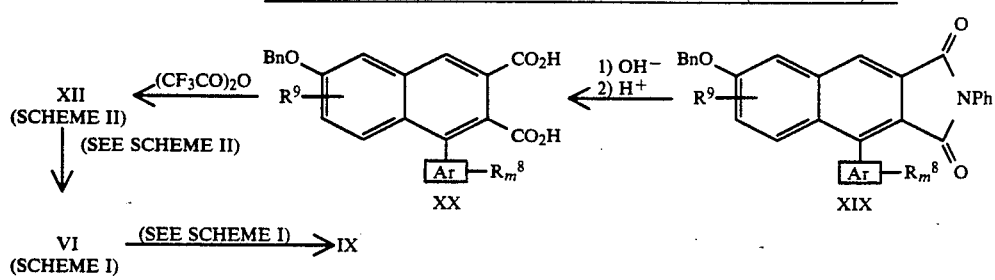
SCHEME V
PREPARATION OF FINAL PRODUCTS
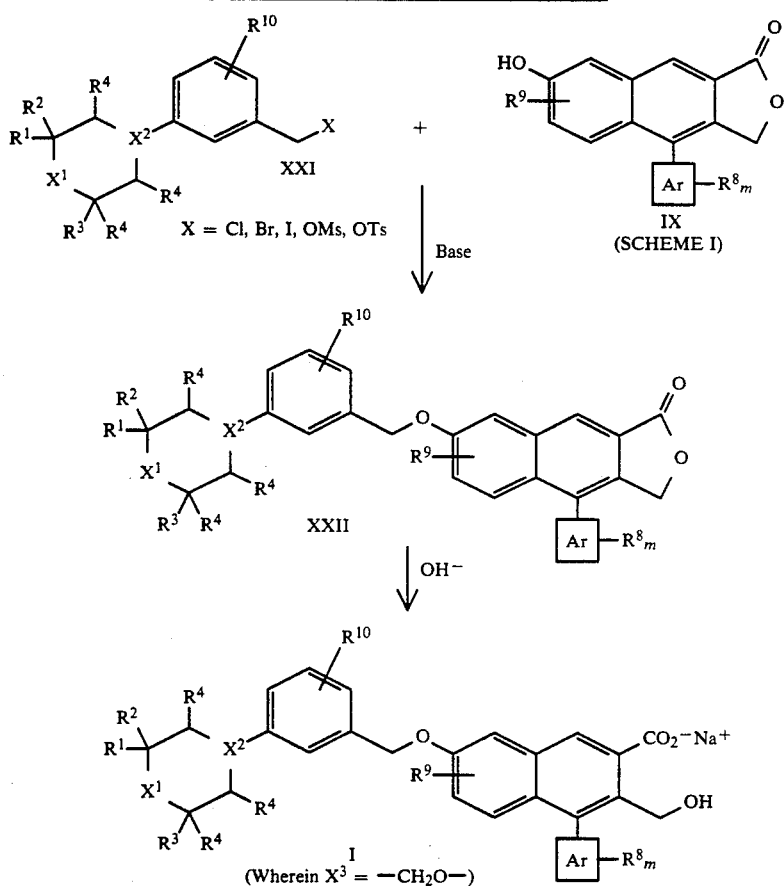
SCHEME VI
PREPARATION OF FINAL PRODUCTS
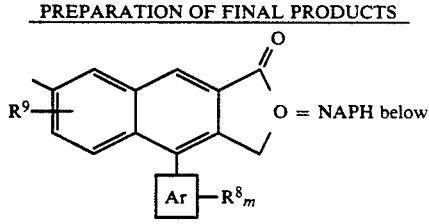
-continued
SCHEME VI
PREPARATION OF FINAL PRODUCTS
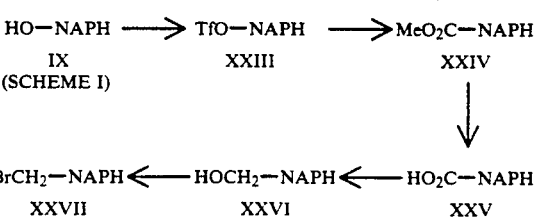

-continued
SCHEME VI
PREPARATION OF FINAL PRODUCTS
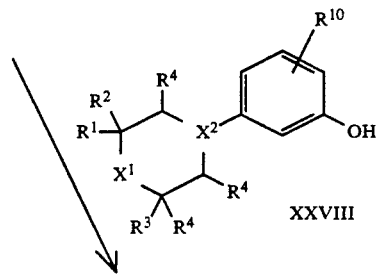
XXVIII
-continued
SCHEME VI
PREPARATION OF FINAL PRODUCTS
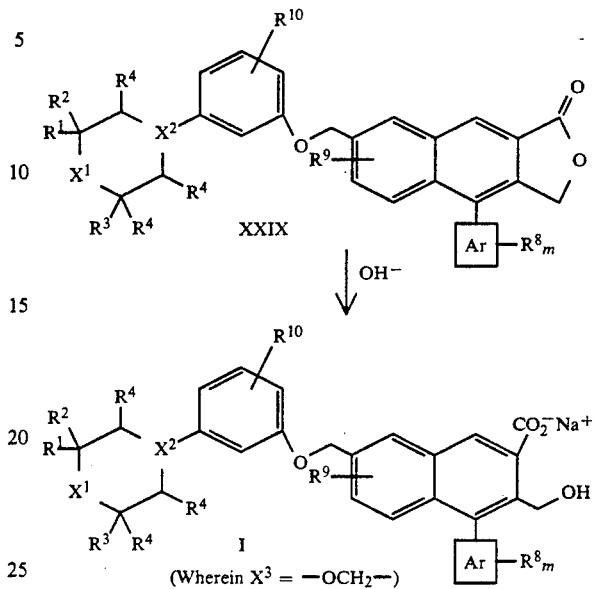
(Wherein $X^3 = -OCH_2-$)
SCHEME VII
PREPARATION OF FINAL PRODUCTS
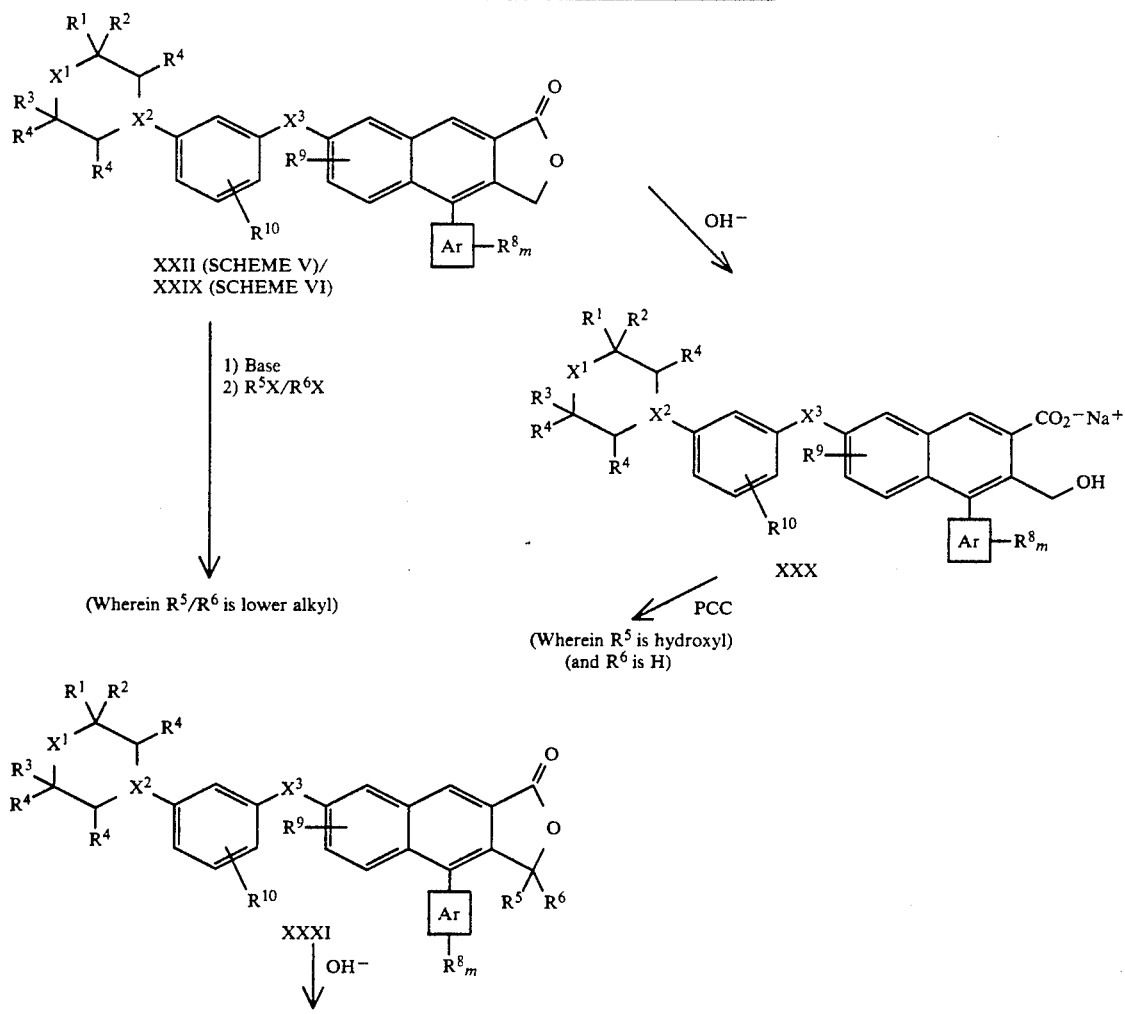

-continued
SCHEME VII
PREPARATION OF FINAL PRODUCTS

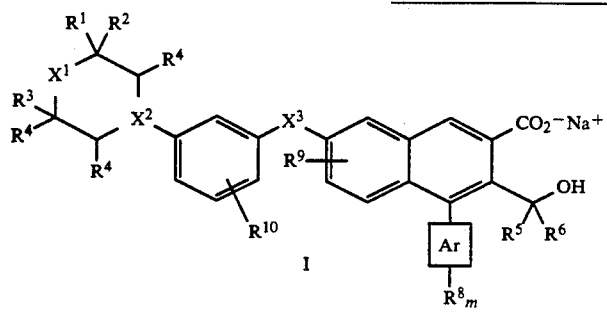

SCHEME VIII
PREPARATION OF LACTONE INTERMEDIATES (METHOD E)

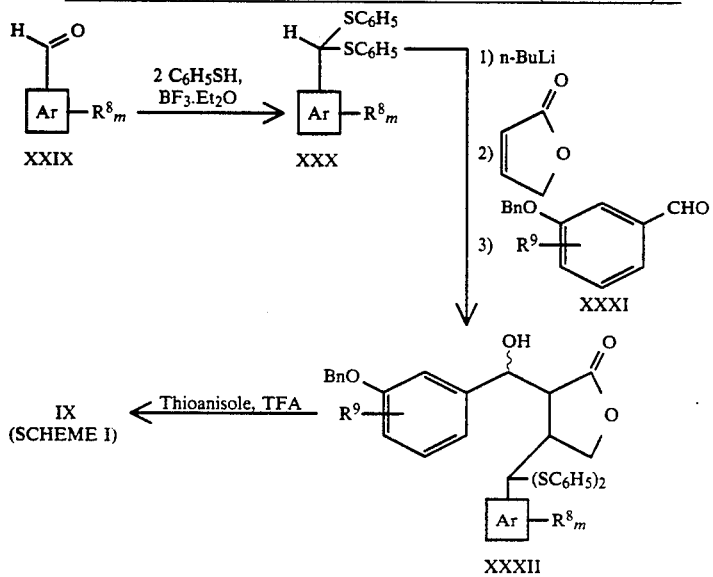

Representative Compounds

Tables 1 and 2 illustrate compounds of Formulas Ia and Ib, which are representative of the present invention.

TABLE 1

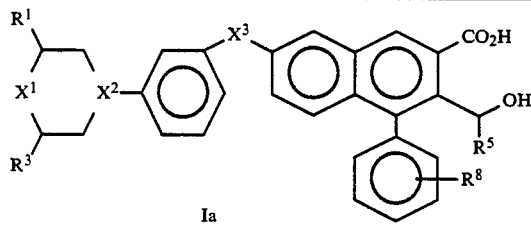

Ia

| Ex. | $R^1$ | $R^3$ | $R^5$ | $R^8$ | $X^1$ | $X^2$ | $X^3$ |
|---|---|---|---|---|---|---|---|
| 1 | H | H | H | H | O | C(OMe) | $CH_2O$ |
| 2 | H | H | H | H | O | C(OMe) | $OCH_2$ |
| 3 | H | H | H | 4-F | O | C(OMe) | $CH_2O$ |
| 4 | H | H | H | H | O | C(OH) | $CH_2O$ |
| 5 | H | H | H | H | O | C(OEt) | $CH_2O$ |
| 6 | H | H | H | H | $CH_2$ | C(OMe) | $CH_2O$ |
| 7 | H | H | H | H | O | N | $CH_2O$ |
| 8 | H | H | H | H | O | N(O) | $CH_2O$ |
| 9 | H | H | OH | H | O | C(OMe) | $CH_2O$ |
| 10 | OH | H | H | H | O | C(OMe) | $CH_2O$ |
| 11 | OH | H | H | H | O | C(OH) | $CH_2O$ |

TABLE 1-continued

Ia

| Ex. | R$^1$ | R$^3$ | R$^5$ | R$^8$ | X$^1$ | X$^2$ | X$^3$ |
|---|---|---|---|---|---|---|---|
| 12 | H | H | OH | H | O | C(OH) | CH$_2$O |
| 13 | OH | H | OH | H | O | C(OH) | CH$_2$O |
| 14 | H | H | Me | H | O | C(OMe) | CH$_2$O |
| 15 | OH | H | OH | H | O | C(OMe) | CH$_2$O |
| 16* | Me | Me | H | H | O | C(OH) | CH$_2$O |
| 17* | Me | Me | H | H | O | C(OH) | CH$_2$O |
| 18 | H | H | H | 4-Cl | O | C(OH) | CH$_2$O |
| 19 | H | H | H | 4-OMe | O | C(OH) | CH$_2$O |
| 20 | Me | Me | H | H | O | C(OMe) | CH$_2$O |
| 21 | H | H | H | H | S | C(OH) | CH$_2$O |
| 22 | H | H | H | H | S(O) | C(OH) | CH$_2$O |
| 23 | H | H | H | H | S(O)$_2$ | C(OH) | CH$_2$O |
| 24** | OMe | H | H | H | O | C(OH) | CH$_2$O |
| 25** | OMe | H | H | H | O | C(OH) | CH$_2$O |
| 26 | H | H | H | H | O | C(Me) | CH$_2$O |
| 27 | H | H | Me | H | O | C(OH) | CH$_2$O |
| 28 | H | H | H | 4-F | O | C(OH) | CH$_2$O |
| 29 | H | H | H | H | O | C(Et) | CH$_2$O |
| 30 | H | H | H | 2-F | O | C(OH) | CH$_2$O |
| 31 | H | H | H | 2-Cl | O | C(OH) | CH$_2$O |
| 32 | H | H | H | 3-OMe | O | C(OH) | CH$_2$O |
| 33** | OCH(Me)$_2$ | H | H | H | O | C(OH) | CH$_2$O |
| 34** | OCH(Me)$_2$ | H | H | H | O | C(OH) | CH$_2$O |
| 35 | (R$^1$R$^3$)= | —CH=CH— | H | H | O | C(OH) | CH$_2$O |
| 36 | (R$^1$R$^3$)= | —CH$_2$CH$_2$— | H | H | O | C(OH) | CH$_2$O |

*cis and trans isomers
**axial and equatorial isomers

TABLE 2

Ib

| Ex. | R$^1$ | R$^2$ | R$^3$ | R$^4$ | R$^5$ | R$^6$ | R$^9$ | R$^{10}$ | X$^1$ |
|---|---|---|---|---|---|---|---|---|---|
| 37 | H | H | H | H | H | H | H | 4-Ome | O |
| 38 | H | H | H | H | Me | Me | H | H | O |
| 39 | H | H | H | H | H | H | 1-OMe | H | O |
| 40 | Me | Me | Me | Me | H | H | H | H | S |
| 41 | (R$^1$R$^2$)= | =O | H | H | H | H | H | H | O |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation (A$_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing the coding region sequence for human 5-lipoxygenase is prepared as described below. The enzymatic activity is measured, using a spectrophotometric assay from the optimal rate of conjugated diene formation ($A_{234}$) using the procedure described by Riendeau et al. (Biochem. Pharmacol., 31, 2323-2321, 1989) with minor modifications. The incubation mixture contains 50 mM sodium phosphate pH 7.4, 0.2 mM ATP, 0.2 MM $CaCl_2$, 20 μM arachidonic acid (5 μl from a 100-fold concentrated solution in ethanol), 12 μg/ml phosphatidylcholine, an aliquot of the 100,000×g fraction (2-10 μl) and inhibitor (0.5 ml final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 ml capacity, 10 mm path length and 4 mm internal width) and the absorbance changes are recorded with a Hewlett-Packard diode array spectrophotometer (HP 8452A) connected to the ChemStation using UV/VIS Kinetics Software. Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time, and $A_o$ is the absorbance at zero time. The results are expressed as percentages of inhibition of the reaction rate relative to controls (typically between 0.15-0.21 AU/min) containing the DMSO vehicle.

Preparation of Lysates from Infected Cells: S19 cells are grown at 27° C. in 100 ml-spinner flasks to a cell density of $1.5-2 \times 10^6$ cells/ml and infected for 44-48 hours with rvH5LO(8-1). The cells are then collected by centrifugation (900×g for 10 min, at 20° C.), washed twice with Dulbacco's phosphate-buffered saline (pH 7.4) ($25 \text{ ml}/2 \times 10^8$ cells) and resuspended at $1.2 \times 10^7$ cells/ml in a homogenization buffer containing 50 MM potassium phosphate (pH 7.9) 2 mM EDTA, 1 mM dithiothreitol, 0.5 mM phenylmethylsulfonyl fluoride and 60 μg/ml soybean trypsin inhibitor. The cells are then lysed by sonication at 4° C. using a Cole Parmer (4710 Series) Ultrasonic homogeniser (3 to 5 bursts of 10 sec. with 30-sec. lags, pulse mode, 70% duty cycle, and output setting at 3). The preparations are examined under the microscope to achieve efficient cell lysis (>90%) with minimal sonication. The lysate is then centrifuged at 100,000×g for 1 hour (Beckman L5-65, 60 Ti rotor) at 4° C. and the resulting supernatant (S-100 fraction) brought to 24 μg/ml PC by the addition of a 250-fold concentrated solution in ethanol. The S-100 fraction (1-3 mg/ml) is stable for several hours at 4° C. and can be stored for several months at −70° C. in 20% ethylene glycol with about 50% recovery of activity.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mM HEPES adjusted to pH 7.4 with NAOH). The cells are pelleted (350×g, 5 min.), resuspended in buffer with vigorous shaking, filtered through lens paper, recentrifuged and finally suspended in buffer at a concentration of 10 cells/ml. A 500 mL aliquot of PMN suspension and test compound are preincubated for 2 minutes at 37° C., followed by the addition of 10 MM A-23187. The suspension is stirred for an additional 4 minutes then bioassayed for $LTB_4$ content by adding an aliquot to a second 500 mL portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Human Polymorphonuclear (PMN) Leukocyte $LTB_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13 M) or 5% (v/v) sodium heparin (1000 IU/mi). PMNs are isolated from anticoagulated blood by dextran sedimentation of erythrocytes followed by centrifugation through Ficoll-Hypaque (specific gravity 1.077), as described by Boyum.[1] Contaminating erythrocytes are removed by lysis following exposure to ammonium chloride (0.16 M) in Tris buffer (pH 7.65), and the PMNs resuspended at $5 \times 10^5$ cells/ml in HEPES (15 mill)-buffered Hanks balanced salt solution containing $Ca^{2+}$ (1.4 mM) and $Mg^{2+}$ (0.7 mill), pH 7.4.

(1) Boyum, A. Scand. J. Clin. Lab. Invest, 1968, 21 (Supp. 97), 77.

B. Generation and Radioimmunoassay of $LTB_4$. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore A23187 (final concentration 10 MM) or vehicle in control samples and allowed to proceed for 5 minutes at 37° C. The reactions are then terminated by the addition of cold methanol (0.25 mi) and samples of the entire PMN reaction mixture removed for radioimmunoassay of $LTB_4$.

Samples (50 mi) of authentic $LTB_4$ of known concentration in radioimmunoassay buffer (RIA) buffer (potassium phosphate 1 mM; disodium EDTA 0.1 mM; Thimerosal 0.025 mm; gelatin 0.1%, pH 7.3) or PMN reaction mixture diluted 1:1 with RIA buffer are added to reaction tubes. Thereafter [$^3$H]-$LTB_4$ (10 nCi in 100 mL RIA buffer) and $LTB_4$-antiserum (100 mL of a 1:3000 dilution in RIA buffer) are added and the tubes vortexed. Reactants are allowed to equilibrate by incubation overnight at 4° C. To separate antibody-bound from free $LTB_4$, aliquots (50 mi) of activated charcoal (3% activated charcoal in RIA buffer containing 0.25% Dextran T-70) are added, the tubes vortexed, and allowed to stand at room temperature for 10 minutes prior to centrifugation (1500×g; 10 min; 4° C.). The supernatants containing antibody-bound $LTB_4$ are decanted into vials and Aquasol 2 (4 mi) added. Radioactivity is quantified by liquid scintillation spectrometry. The specificity of the antiserum and the sensitivity of the procedure have been described by Rokach &t al.[2] The amount of $LTB_4$ produced in the test and control samples is calculated. Inhibitory dose-response curves are constructed using a four-parameter algorithm and from these the $IC_{50}$ values determined.

(2) Rokach, J.; Hayes, E. C.; Girard, Y.; Lombardo, D. L.; Maycock, A. L.; Rosenthanl, A. S.; Young, R. N.; Zamboni, R.; Zweerink, H. J. Prostaglandins Leukotrienes and Medicine, 1984, 13, 21.

Human Whole Blood Assay in Vitro for LTB$_4$ Production

A. Blood

Blood (60 ml) is collected from male volunteers directly into 10 ml heparinized vacutainers for assay; one volunteer per assay.

B. Test Compounds

Stock solution: Most concentrated working solution (final) multiplied by the dilution factor (volume of compound vs blood volume); e.g., 60 μM dose ×500 (DMSO 1/500) = 30 mM stock solution. To calculate the amount of compound needed to make stock solution: mol. wt. of drug × 1/1000 × stock concentration; e.g., 618 × 1/1000 × 30 MM = 18.54 mg for 1 ml vehicle either DMSO or methanol.

Working Solutions: Serial dilutions of stock with appropriate vehicle. If methanol is used to dissolve compound, then use methanol/BSA solution to dilute the stock. Methanol/BSA = 1 ml 100% methanol = 9 ml BSA 1 mg/ml saline.

Effective conc. in the assay depends upon the test compound (may be 60 uM to 0.1 uM). 1/500 dilution for DMSO vehicle 1 μl for 500 μl blood. 1/50 dilution for MEOH/BSA 10 μl for 500 μl blood.

C. A23187

50 mM stock solution: 50 mg A23187 for 1.9 ml DMSO in 50 μl aliquots (stored at −20° C.).

Working Solution: 40 μl of 50 MM stock + 760 μl homologous plasma = 2.5 mM solution vehicle plasma.

Effective conc. in assay should be 25 μM (1/100 dilution).

D. Assay

Add 1 μl (DMSO) of 10 μl (MeOH/BSA) of either test compound or vehicle (use 10 μl hamilton syringe to deliver 1-10 μl) to properly labelled 1.5 ml Eppendorf tubes. 500 μl of blood is dispensed into each tube, which is then vortexed, transfered to a plastic box with lid, washed outside with methanol and incubated 15 min. at 37° C. Meanwhile, centrifuge ~2 ml blood in microfuge at 12,000×g for 5 minutes to obtain plasma for the A23187 solution. At the end of the 15 minutes incubations, add 5 μl of the 2.5 MM A23187 working solution or 5 μl of plasma (blanks) into each tube. Vortex well and incubate for 30 minutes at 37° C. At the end of the last incubation, the plasma is obtained by centrifugation as described above, and a 100 μl aliquot is placed into 400 μl of 100% methanol. Meanwhile, transfer the remaining 150 μl of plasma into a clean Eppendorf tube and the store at −70° C. The samples are vortexed and centrifuged as before. The supernatant (methanol extract) is stored at −70° C. until RIA for LTB$_4$ (20 μl aliquot) as in the above human PMN assay.

SAMPLES

| | |
|---|---|
| 2 blanks | = 500 μl blood + 1 or 10 μl vehicle + 5 μl plasma |
| 4 controls | = 500 μl blood + 1 or 10 μl vehicle + 5 μl A23187 |
| 2 drug blanks | = 500 μl blood + 1 or 10 μl highest conc. of drug + 5 μl plasma |
| X drugs | = 500 μl blood + 1 or 10 μl drug + 5 μl A23187 |

Asthmatic Ray Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10 ×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of Methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an ED$_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 ml/kg body weight. For aerosol administration of compounds, a DeVilbiss ultrasonic nebulizer is utilized. Pretreatment periods vary from 5 minutes to 4 hours before the monkeys are challenged with aerosol doses of Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of Ascaris antigen response by the test compound. For statistical analysis, paired t-test is used. (References: McFarlane, C. S. it al., Prostaglandins, 28:173-1829 1984, McFarlane, C. S. it al., Agents Actions 22:63-68, 1987.)

Prevention of Induced Bronchoconstriction in Allergic Sheep

A. Rationale. Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods. Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, NC) and b) they have previously responded to inhalation challenge with *Ascaris suum* with both an acute bronchoconstriction and a late bronchial obstruction (Abraham, W. M. Delehunt, J. C., Yerger, L. and Merchette, B., Am. Rev. Resp. Dis., 1983, 128, 839-44).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop ®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5-1 hr prior to Ascaris challenge and for 8 hrs after Ascaris as described above.

Statistical Analysis A Kruskal-Wallis one way ANOVA test is used to compare the acute immediate responses to antigen and the peak late response in the controls and the drug treated animals.

PREPARATION OF BENZYL HALIDES

Halide 1: 3-[4-(4-Methoxy)tetrahydropyranyl]benzyl bromide

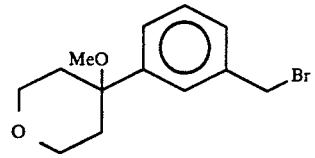

Step 1: 3-[4-(4-Hydroxy)tetrahydropyranyl]toluent

To a solution of 3-bromotoluene (24.3 mL; Aldrich) in THF (250 mL) stirred at −78° C. was added a solution of n-butyl lithium in hexane (1.75M; 114 mL; Aldrich). After 45 min., the resulting white suspension was treated with a solution of tetrahydropyran-4-one (18.5 mL; Aldrich) in THF (125 mL). After 45 min. at −78° C., the mixture was stirred for 1.5 h at room temperature. Saturated aqueous NH4Cl was then added and the organic phase separated. The aqueous phase was extracted with EtOAc. The combined organic phases were washed with brine, dried (MgSO4) and evaporated. Flash chromatography of the residue (silica gel; hexane/EtOAc (1:1)) followed by crystallization in hexane/EtOAc afforded the title compound as a white solid.

Step 2: 3-[4-(4-Methoxy)tetrahydropyranyl]toluene

To a 0° C. solution of the alcohol (38 g; Step 1) in DMF (300 mL) were added NaH (60% in mineral oil; 16 g) and methyl iodide (31 mL). The mixture was stirred under nitrogen at room temperature for 15 hours before water (1 L) was added. The aqueous phase was extracted with EtOAc and the combined organic phases were washed with brine, dried (MgSO₄) and evaporated. Flash chromatography of the residue (silica gel; hexane/EtOAc (4:1)) yielded the title ether as a colorless liquid.

Step 3: 3-[4-(4-Methoxy)tetrahydropyranyl]benzyl bromide

A mixture of the toluene (16 g) from Step 2, N-bromosuccinimide (14.6 g) and azoisobutyronitrile (AIBN) (127 mg) in CCl₄ (250 mL) was refluxed for 1.5 hours. Filtration and evaporation of the filtrate gave the desired benzyl bromide.

Halide 2: 3-[4-(4-Hydroxy)tetrahydropyranyl]-benzyl bromide

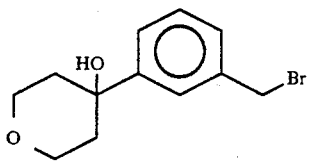

Following the procedure described for Halide 1, Step 3, but substituting 3-[4-(4-hydroxy)tetrahydropyranyl]-toluene (from Halide 1, Step 1) for 3-[4-(4-methoxy)tetrahydropyranyl]toluene, the title product was obtained as a yellow oil.

Halide 3: 3-[4-(4-Ethoxy)tetrahydropyranyl]benzyl bromide

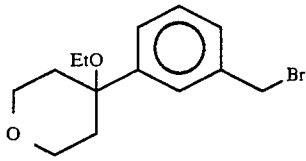

Step 1: 3-[4-(4-Ethoxy)tetrahydropyranyl]toluene

A solution of 3-[4-(4-hydroxy)tetrahydropyranyl]toluene (Halide 1, Step 1) (368 mg) in DMSO (5 mL) was treated with powdered KOH (490 mg) and ethyl iodide (0.38 mL). After the mixture had been stirred at room temperature for 22 hours, ether (25 mL) was added. The organic phase was then washed with water (2×25 mL) and brine, dried (MGSO₄), and evaporated. Flash chromatography of the residue (silica gel; hexane/EtOAc, (85:15)) afforded the title product as a colorless liquid.

Step 2: 3-[4-(4-Ethoxy)tetrahydropyranyl]benzyl bromide

Following the procedure described in Halide 1, Step 3, but substituting the toluene from Halide 3, Step 1 for 3-[4-(4-methoxy)tetrahydropyranyl)toluene, the title benzyl bromide was obtained as an oil.

Halide 4: 3-(1-Methoxycyclohexyl)benzyl bromide

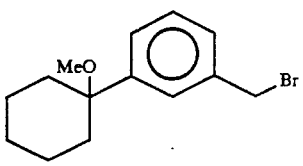

Following the procedure described in Halide 1, Steps 1-3 but substituting cyclohexanone for tetrahydropyran-4-one, the title product was obtained as a liquid.

Halide 5: 3-(N-Morpholino)benzyl chloride

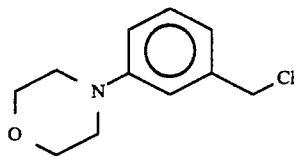

Step 1: Ethyl 3-(N-morpholino)benzoate

In a glass pressure vessel containing a magnetic stirrer was placed morpholine (8.7 g; 100 mmol), ethyl 3-bromobenzoate (20.6 g; 90 mmol), cupric oxide (0.79 g; 10 mmol), potassium carbonate (13.8 g; 100 mmol) and pyridine (20 mL). The vessel was closed and heated under pressure at 175° C. for 18 hrs. The mixture was cooled and stirred with water and diethyl ether. The organic layer was separated, washed with water, 1N hydrochloric acid, dried (MgSO₄), filtered and concentrated. The residue was chromatographed on silica gel using 15% ethyl acetate in hexane to obtain the title compound in low yield as an oil.

Step 2: 3-(N-Morpholino)benzyl alcohol

To a solution of ethyl 3-(N-morpholino)benzoate (432 mg; 1.8 mmol) in THF (15 mL) at 0°-5° C. was added lithium aluminum hydride (209 mg; 5.5 mmol) in portions under a nitrogen atmosphere. After stirring for 30 min., excess water was added dropwise; Diethyl ether and 1N sodium hydroxide were then added. The organic layer was seperated, dried (MgSO₄), filtered and concentrated to obtain the title compound as an oil which was used as such in the next reaction.

Step 3: 3-(N-Morpholino)benzyl chloride

To a solution of 3-(N-morpholino)benzyl alcohol (265 mg; 1.3 mmol) and hexamethyl phosphorus triamide (502 μL; 2.7 mmol) in dichloromethane (10 mL) was added at room temperature carbon tetrachloride (280 KL; 2.7 mmol). The mixture was stirred for 15 minutes and then concentrated. Diethyl ether was added to the residue and the mixture filtered through celite. The filtrate was concentrated and the residue chromatographed on silica gel using 30% ethyl acetate in hexane to obtain the title compound. m.p. 52°-55° C.

Halide 6:
3-[4-(4β3-Hydroxy-2,6-dimethyl)tetrahydropyranyl]-benzyl bromide

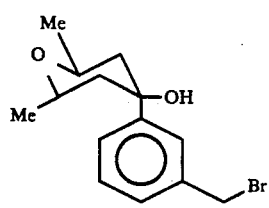

Step 1: 3-Bromo-O-tetrahydropyranylbenzyl alcohol

To a solution of 3-bromobenzyl alcohol (11.5 g; Aldrich) dissolved in CH$_2$Cl$_2$ (100 mL) at 0° C. and p-toluenesulfonic acid monohydrate (116 mg) was added 6.2 mL of DHP. The resulting solution was stirred at r.t. for 3 hr. then was quenched with NH$_4$OAc. The aqueous phase was extracted with CH$_2$Cl$_2$. The combined organic phases were washed with brine, dried (MgSO$_4$) and evaporated. Flash chromatography of the residue (silica gel; hexane/EtOAc, 9:1) afforded the title compound as an oil.

Step 2: 2.6-Dimethyltetrahydropyran-4-one

A solution of 2,6-dimethyl-γ-pyrone (17 g) in 300 mL of ETOH 95% was hydrogenated for 3 days under 70 psi. After filtration over celite, without extraction, the solvent was evaporated and replaced by CH$_2$Cl$_2$. The solution was then treated with 30 g of celite and 48.5 g of pyridinium chlorochromate. The suspension was stirred for 3 hr. and the reaction was diluted with 300 mL of Et$_2$O and then filtered over a pad of celite. The filtrate was evaporated to dryness and the residual solution was then chromatographed using hexane/ether (1:1) to give the title compound.

Step 3: 3-[4-(4l3-Hydroxy-2,6-dimethyl)tetrahydropyranyl]-O-tetrahydropyranylbenzyl alcohol Following the procedure described in Halide 1, Step 1, but substituting 3-bromo-0-tetrahydropyranylbenzyl alcohol from Halide 6, Step 1 for 3-bromotoluene and substituting 2,6-dimethyltetrahydropyran-4-one from Halide 6, Step 2 for tetrahydropyran-4-one, the title Compound was obtained as a mixture of a and β isomers (30:70). Both isomers could be isolated from a flash column (hexane/EtOAc, 6:4). The β-hydroxy isomer is more polar than the α-hydroxy isomer.

Step 4: 3-[4-(4β-Hydroxy-2,6-dimethyl)tetrahydropyranyl]benzyl alcohol

The β-hydroxy-THP derivative (1.0 g) obtained in Halide 6, Step 3, was dissolved in 10 mL of ETOH and treated with 30 mg of p-toluenesulfonic acid. The reaction was stirred at r.t. for 90 min. The ETOH was evaporated and the resulting syrup was flash chromatographed to give the title compound.

Step 5: 3-[4-(4β-Hydroxy-2,6-dimethyl)tetrahydropyranyl]benzyl bromide

To a solution of alcohol (183 mg) from Halide 6, Step 4, in CH$_2$Cl$_2$ (9 mL) was added 269 mg of CBr$_4$. The reaction was then cooled at −30° C. and 298 mg of DIPHOS was added in portions. After 10 min., the reaction was quenched with a solution (10 mL) of 10% EtOAc in hexane and without evaporation, the solvent was poured onto a silica gel column and eluted with EtOAc/hexane (3:7). The title compound was isolated and used immediately in the next step.

Halide 7:
3-[4-(4α-Hydroxy-2,6-dimethyl)tetrahydropyranyl]benzyl bromide.

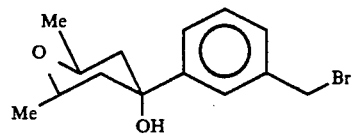

Step 1: 3-[4-(4a-Hydroxy-2,6-dimethyl)tetrahydropyranyl]benzyl alcohol

Following the procedure described in Halide 6, Step 4, but substituting α-hydroxy-THP derivative from Halide 6, Step 3, for β-hydroxy-THP derivative, the title product was obtained.

Step 2: 3-[4-(4α-Hydroxy-2,6-dimethyl)tetrahydropyranyl]benzyl bromide

Following the procedure described in Halide 6, Step 5, but substituting the α-hydroxy alcohol derivative from Halide 7, Step 1 for the β-hydroxy alcohol derivative, the title compound was obtained.

Halide 8:
3-[4-(4-Hydroxy-2-methoxy)tetrahydropyranyl]benzyl bromide

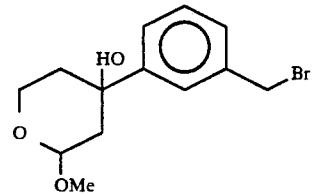

Step 1: 3-F4-(4-Hydroxy-2.3-dihydropyranyl)toluene

Following the procedure described in Halide 1, Step 1, but substituting 2,3-dihydro-4H-pyran-4-one (J. Org. Chem., 49, 1955 (1984)) for tetrahydropyran-4-one, the title compound was obtained as an oil.

Step 2: 3-[4-(3-Bromo-4-hydroxy-2-methoxy)tetrahydropyranyl]toluene

To a cold (10° C.) solution of the alcohol (1.45 g) from Step 1 in MEOH (15 mL) was added NBS (1.36 g) and the resulting mixture stirred for 40 minutes. A phosphate buffer solution (pH 7, 50 mL) was added to the reaction mixture and extracted with CH$_2$Cl$_2$ (3×25 mL). The organic layers were dried over MgSO$_4$ and evaporated to dryness. Flash chromatography of the residue (silica gel; hexane/EtOAc, 80:20) afforded the title product as an oil.

Step 3:
3-[4-(4-Hydroxy-2-methoxy)tetrahydropyranyl]-toluene

A mixture of the bromo alcohol (480 mg) from Step 2, tributyltinhydride (0.43 mL) and AIBN (2 mg) in toluene (3 mL) was refluxed under nitrogen for 2 hours. After evaporation, the resulting residue was dissolved in CH₃CN (20 mL) and washed with hexane (3×10 mL). The acetonitrile layer was evaporated to dryness and the resulting residue was purified by flash chromatography (silica gel; hexane/EtOAc, 85:15) to afford the title compound as an oil.

Step 4:
3-[4-(4-Hydroxy-2-methoxy)tetrahydropyranyl]-benzyl bromide

Following the procedure described for Halide 1, Step 3, but substituting 3-[4-(4-hydroxy-2-methoxy)tetrahydropyranyl]toluene from Step 3 for 3-[4-(4-methoxy)tetrahydropyranyl]toluene, the title product was obtained as an oil.

Halide 9: 3-[4-(4-Methyl)tetrahydropyranyl]benzyl bromide

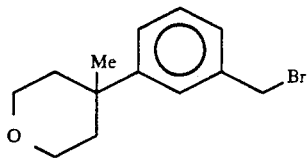

Step 1: 3-F4-(4-Chloro)tetrahydropyranyl]toluene

A solution of 3-[4-(4-hydroxy)tetrahydropyranyl]toluene (Halide 1, Step 1) (0.57 g in CHCl₃ (10 mL)) was added to a slurry of P₂Cl₅ (1.92 g) and K₂CO₃ (0.41 g) in CHCl₃ (10 mL) and stirred at 0° C. for 35 min. The reaction mixture was filtered. Evaporation of the filtrate afforded the title compound as a yellow semi-solid.

Step 2: 3-r4-(4-Methyl)tetrahydropyranyl]toluene

To a 0° C. solution of the chloride (452 mg; Step 1) in CH₂Cl₂ (7 mL) was added a solution of trimethylaluminum in hexane (2.0 M; 2.2 mi; Aldrich). The mixture was stirred at room temperature for 19 hours before saturated NaHCO₃ was added. The aqueous phase was extracted twice with CH₂Cl₂ and the combined organic phases were dried (MgSO₄) and evaporated. Flash chromatography of the residue (silica gel; hexane/EtOAc, 9:1) yielded the title compound as a colorless liquid.

Step 3: 3-[4-(4-Methyl)tetrahydropyranyl]benzyl bromide

Following the procedure described in Halide 1 Step 3, but substituting the toluene from Halide 8, Step 2, for 3-[4-(4-methoxy)tetrahydropyranyl)toluene, the title product was obtained as an oil.

Halide 10: 3-[4-(4-Ethyl)tetrahydropyranyl]benzyl bromide

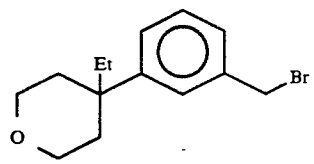

Following the procedure described in Halide 9, Steps 2–3, but substituting triethylaluminum for trimethylaluminum, the title benzyl bromide was obtained as an oil.

Halide 11:
3-[4-(4α-Hydroxy-2,2,6,6-tetramethyl)tetrahydrothiopyranyl]benzyl chloride

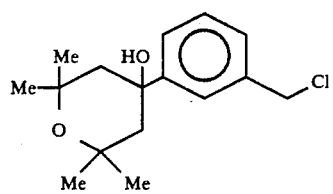

Step 1:
3-[4-(4α-Hydroxy-2,2,6,6-tetramethyl)tetrahydrothiopyranyl]-O-tetrahydropyranylbenzyl alcohol Following the procedure described in Halide 1 Step 1, but substituting 3-bromo-O-tetrahydropyranylbenzyl alcohol (Halide 6, Step 1) for 3-bromotoluene and tetrahydro-2,2,6,6-tetramethylthiopyran-4-one (J. Org. Chem. 43, 331 (1978)) for tetrahydropyran-4-one, the title compound was obtained. Step 2: 3-[4-(4α-Hydroxy-2,2,6,6-tetramethyl)tetrahydrothiopyranyl]benzyl alcohol A solution of the THP derivative (1.5 g) from Step 1, in 20 mL of ETOH and pyridinium p-toluenesulfonate (39 mg) was heated at 55° C. for 3 hours. Evaporation of the solvent followed by a flash column (hexane/EtOAc, 7:3) gave the title compound.

Step 3:
3-[4-(4a-Hydroxy-2,2,6,6-tetramethyl)tetrahydrothiopyranyl]benzyl chloride To a solution of the alcohol (500 mg) from Step 2, in CH₂Cl₂ (20 ml) and CCl₄ (250 KL) was added Ph₃P (515 mg). The reaction was heated overnight at 70° C. Then the reaction was diluted with 10% EtOAc in hexane and flash chromatographed directly to give the title compound.

Halide 12:
3-[4-(4-Hydroxy)tetrahydrothiopyranyl]benzyl chloride

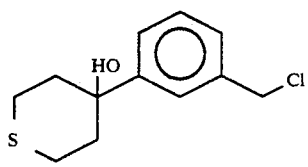

Step 1: 3-[4-(4-Hydroxy)tetrahydrothiopyranyl]-O-tetrahydropyranylbenzyl alcohol Following the procedure described in Halide 1 Step 1, but substituting 3-bromo-O-tetrahydropyranylbenzyl alcohol from Halide 6, Step 1, for 3-bromotoluene and substituting tetrahydrothiopyran-4-one (Aldrich) for tetrahydropyran-4-one, the title compound was obtained.

Step 2: 3-[4-(4-Hydroxy)tetrahydrothiopyranyl]benzyl alcohol

Following the procedure described in Halide 6, Step 4, but substituting the THP derivative from Step 1 for the β-hydroxy-THP derivative, the title product was obtained.

Step 3: 3-[4-(4-Hydroxy)tetrahydrothiopyranyl]benzyl chloride

To a solution of the alcohol (572 mg, 2.3 mmol) from Step 2, in CH$_2$Cl$_2$ (20 mL) and CCl$_4$ (273 μL) was added Ph$_3$P (681 mg). The reaction was heated overnight at 70° C. Then the reaction was diluted with 10% EtOAc in hexane and flash chromatographed directly to give the title compound.

Halide 13: 3-[3-(8-oxabicyclo[3.2.1]oct-6-en-3α-ol)benzyl chloride

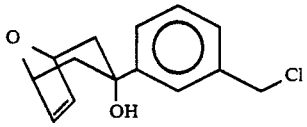

Step 1: 3-[3-(8-Oxabicyclo[3.2.1]oct-6-en-3α-ol)-O-tetrahydropyranylbenzyl alcohol Following the procedure described in Halide 1, Step 1, but substituting 3-bromo-O-tetrahydropyranylbenzyl alcohol from Halide 6, Step 1, for 3-bromotoluene and substituting 8-oxabicyclo[3.2.1]-oct-6-en-3-one (J. Amer. Chem. Soc. 100, 1765 (1978)) for tetrahydropyran-4-one, the title compound was obtained.

Step 2: 3-[3-(8-Oxabicyclo[3.2.1]oct-6-en-3α-ol)benzyl alcohol

Following the procedure described in Halide 11 Step 2, but using the THP derivative from Step 1, the title product was obtained.

Step 3: 3-[3-(8-Oxabicyclo[3.2.1]oct-6-en-3α-ol)benzyl chloride

To a solution of the alcohol (300 mg, 1.3 mmol) obtained from Step 2, in CH$_2$Cl$_2$ (5 mL) and CCl$_4$ (144 μL) was added Ph$_3$P (407 mg). The reaction was heated overnight at 70° C. The reaction was diluted with 10% EtOAc in hexane and flash chromatographed directly to give the title compound.

Halide 14: 3-[3-(8-Oxabicyclo[3.2.1]octan-3α-ol]-benzyl bromide

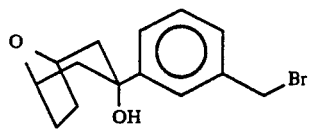

Step 1: 3-[3-(8-Oxabicyclo[3.2.1]oct-6-en-3α-ol)]-toluene

Following the procedure described in Halide 1, Step 1, but substituting 8-oxabicyclo[3.2.1]oct-6-en-3-one (J. Amer. Chem. Soc. 100, 1765 (1978)) for tetrahydropyran-4-one, the title compound was obtained.

Step 2: 3-[3-(8-Oxabicyclo[3.2.1]octan-3α-ol)]-toluene

A mixture of the bicyclic alkene (1.50 g) from Step 1 and 10% Pd/C on carbon (0.5 g) in EtOAc (150 mL) and MEOH (15 mL) was stirred under hydrogen at r.t. for 18 hours. The reaction mixture was then filtered over celite and evaporation of the filtrate afforded a yellow waxy solid. Trituration in ether followed by filtration and evaporation of the filtrate then gave a white solid. Purification by flash chromatography (silica gel; hexane/EtOAc, 3:1) yielded the title toluene.

Step 3: 3-[3-(8-Oxabicyclo[3.2.]octan-3α-ol)]benzyl bromide

A mixture of the toluene (0.39 g) from Step 2, NBS (0.33 g) and benzoyl peroxide (10 mg) in CCl$_4$ (10 mL) was refluxed and irradiated with visible light for 1.5 hours. Filtration and evaporation of the filtrate gave the title benzyl bromide.

Halide 15: 3-[4-(4-Hydroxy)tetrahydropyranyl]-4-methoxybenzyl chloride

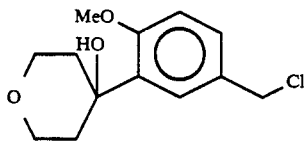

Step 1: 3-Bromo-4-methoxybenzyl alcohol

To a solution of 9.8 g (42 mmol) of 3-bromo-4-methoxybenzoic acid in THF (100 mL) was added 1M solution of borane in THF (130 mL) at r.t. under nitrogen. The resulting solution was then heated at 75° C. for 30 min. The reaction mixture was then cooled to r.t. and MEOH (0.5 mL) was slowly added. The mixture was concentrated and successively treated with MEOH (0.5 mL), evaporated (2×) and finally triturated with Et$_2$O and filtered to yield the title product as a solid, m.p.: 49°–54° C.

Step 2: 3-[4-(4-Hydroxy)tetrahydropyranyl]-4-methoxybenzyl alcohol

To a solution of 9.1 g (42 mmol) of 3-bromo-4-methoxybenzyl alcohol from Step 1 in THF (250 mL) cooled at −78° C. was added n-BuLi (1.6 M, 58 mL) and the resulting solution was stirred for 20 min., then tetrahydropyran-4-one (4.6 g) was added dropwise. The mixture was then allowed to warm to r.t., diluted with brine and extracted with Et₂O. The organic phase was dried over anhydrous MgSO₄ and evaporated. The resulting product was purified by flash chromatography using EtOAc as eluant to give the title product.

Step 3: 3-[4-(4-Hydroxy)tetrahydropyranyl]-4-methoxybenzyl chloride

To a solution of 4.0 g (16.8 mmol) of the corresponding diol from Step 2 in THF (80 mL) was added NaH (887 mg) by portion at r.t. The resulting mixture was stirred for 1 hr then cooled to 5° C. and TsCl (3.8 g) was added. The reaction mixture was then stirred at r.t. and LiCl (3 g) was added and stirred for 1 hr. The resulting mixture was then transferred to a solution of 20% citric acid and extracted with Et₂O. The organic layer was washed with brine, dried over anhydrous MgSO₄, filtered and concentrated. Purification by flash chromatography using 50% EtOAc in hexane gave 900 mg (21%) of the title product, m.p.: 96°–99° C.

PREPARATION OF LACTONES

Lactone 1:
7-Hydroxy-3-hydroxymethyl-4-phenyl-2-naphthoic acid, lactone form

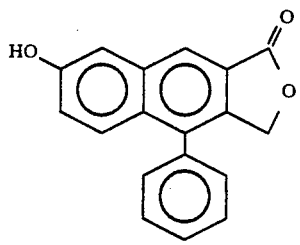

Method A

Step 1: 3-Benzyloxy-β, β-dibromostyrene

To a solution of triphenylphosphine (119.6 g) in methylene chloride (420 mL) at 0° C. was added a solution of carbon tetrabromide (75.72 g) in methylene chloride (90 mL). After completion of the addition, the mixture was stirred for 10 min. Then a solution of 3-(benzyloxy)benzaldehyde (J.A.C.S., 93, 2571 (1977)) (40 g) in methylene chloride (150 ml) was added. The mixture was stirred for 16 hrs at −5° C. After warming to room temperature, the organic layer was washed with saturated sodium bicarbonate (2×150 ml) and brine (1×150 ml), then dried over magnesium sulfate, filtered and the mixture was concentrated. Ether (300 ml) was added, causing the formation of a precipitate which was filtered. The filtrate was concentrated and the process repeated 2 times. Finally, the filtrate was concentrated and chromatographed using 10% ethyl acetate in hexane, affording the title compound as a solid.

Step 2: 3-Benzyloxyphenylpropiolic acid

To a solution of the dibromide from Step 1 (15 g) in tetrahydrofuran (150 ml) at −78° C. was added. slowly n-BuLi (53.4 ml, 1.6 M). Then the mixture was left to warm to 0° C. and stirred at that temperature for 1 hour. Carbon dioxide was bubbled for 10 min. through the mixture which was then diluted with water (150 ml) and 10N NAOH (20 ml). The aqueous layer was washed with ether (2×100 ml), acidified with 6N HCl, and extracted with ethyl acetate (300 ml). The organic layer was washed with brine (2×150 ml), dried over magnesium sulfate, filtered and the solvent evaporated affording the title compound as a solid.

Step 3: 3-Phenylpropargyl 3-benzyloxyphenylproprolate

To a solution of acid (7.5 g) from Step 2 in toluene (123.8 ml) and N,N-dimethylformamide (10 ml) at 0° C. was slowly added oxalyl chloride (2.84 ml). The mixture was stirred for 15 min., then slowly transferred into a solution of 3-phenyl-2-propyn-1-ol (J.O.C., 41, 4089 (1976)) (3.93 g) in tetrahydrofuran (82 ml) and triethylamine (9.94 ml) at OIC. The mixture was stirred for 20 min. then saturated sodium bicarbonate (80 ml) was added, followed by ether (200 ml). The organic layer was washed with brine (2×100 ml), dried over magnesium sulfate, filtered and the solvent evaporated. Purification by chromatography afforded the title compound as a solid.

Step 4: 7-Benzyloxy-3-hydroxymethyl-4-phenyl-2-naphthoic acid, lactone form

A solution of the ester (6 g) from Step 3 in acetic acid (300 ml) was heated to reflux for 6 hours. Then the acetic acid was evaporated. Chromatography on silica gel, eluting with a mixture of EtOAc/CH₂Cl₂/hexane (5:15:80), afforded the title product, m.p. 180°–181° C.

Two side-products were isolated from this reaction: 3-hydroxymethyl-4-phenyl-5-benzyloxy-2-naphthoic acid, lactone form and 3-hydroxymethyl-1-(3-benzyloxyphenyl)-2-naphthoic acid, lactone form.

Step 5: 7-Hydroxy-3-hydroxymethyl-4-phenyl-2-naphthoic acid, lactone form

A solution of the lactone from Step 4 (2.8 g; 7.6 mmol) in acetic acid (80 ml) and 6N hydrochloric acid (15 mL) was refluxed for 7 hours. The mixture was concentrated and then chromatographed using 10% ethyl acetate in toluene to obtain the title compound, m.p. 266°–269° C.

Method B

Step 1: 2-(α-Hydroxybenzyl)-5-benzyloxybenzaldehyde dimethylacetal

To a solution of 2-bromo-5-benzyloxy benzaldehyde dimethylacetal (Tet. Lett., 22, 5027 (1981)) (130 g) in THF (2.0 L), cooled to −78° C., was added dropwise a solution of n-BuLi (210 ml, 1.91 M) in hexane. After 15 min., a solution of benzalde48 mL) in THF (50 ml) was added dropwise. The cooling bath was removed, then the reaction mixture was warmed slowly (40 min.) to −10° C. and quenched with a saturated NH₄Cl solution. The reaction mixture was diluted with Et₂O (2.0 L). The organic phase decanted, washed with H₂O (3×), brine, dried over MgSO₄ and the solvents evaporated. The residue was chromatographed on silica gel (hexane/EtOAc 95:5 to 85:15) to give the title product as a foam.

Step 2:
7-Benzyloxy-4-phenylnaphthalene-2,3-dicarboxylic anhydride

To a solution of the alcohol (112 g) from Step 1 in toluene (1.1 L) was added maleic anhydride (150 g). The reaction mixture was heated to reflux for 24 hours. After cooling to room temperature, the toluene was evaporated. The residue was triturated in EtOAc at 0° C., filtered and washed with Et₂O to afford the title product as a white solid.

Step 3:
7-Benzyloxy-3-hydroxymethyl-4-phenyl-2-naphthoic acid, lactone form To a solution of the anhydride (2 g) from Step 2 in DMF (40 mL) was added a solution of Zn(BH₄)₂ (30 ml of 0.08M in ether) (J.A.C.S.., 6074, 1960). The resulting reaction mixture was heated at 50° C. for 18 hours. After cooling to room temperature, an aqueous solution of 1N HCl was added and the reaction mixture was diluted with ethyl acetate (200 ML), washed with H₂O (2×), brine, dried over MgSO₄, and the solvent evaporated. The reside was purified by chromatography on silica gel using hexane/ethyl acetate 9:1 to first give the title product as the major component, followed by a minor product corresponding to 7-benzyloxy-2-hydroxymethyl-4-phenyl-3-napthoic acid, lactone form.

Use of the title product is described in Method A, Step 5.

Method C

Step 1: 2-Bromo-5-benzyloxybenzaldehydepropane dithioacetal

To a solution of 2-bromo-5-benzyloxy benzaldehyde (Tet. Lett., 22, 5027 (1981)) (51.8 g) in CH₂Cl₂ (400 mL) was added 1,3-propanedithiol (17.5 mL), then BF₃·Et₂O (3 mL). The reaction mixture was stirred at room temperature for 16 hours then quenched with a saturated solution of NH₄Cl. The organic phase was extracted and washed with a saturated solution of sodium bicarbonate, H₂O, brine, dried over MgSO4 and evaporated. The solid residue was recrystallized from hexane/EtOAc to afford the title compound.

Step 2:
7-Benzyloxy-4-phenylnaphthalene-2,3-dicarboxylic anhydride

Following the procedures described in Method B, Steps 1 and 2, but substituting the thioacetal from Method C, Step 1 for 2-bromo-5-benzyloxy benzaldehyde dimethylacetal, the title compound was obtained as a foam.

Use of the title product is described in Method B, Step 3 and Method A, Step 5.

Method D

Step 1: 2-Benzoyl-5-benzyloxybenzaldehyde dimethylacetal

To a solution of 2-bromo-5-benzyloxy benzaldehyde dimethyl acetal (Tet. Lett., 22, 5027 (1981)) (52.2 g) in THF (600 mL), cooled to −78° C., was added dropwise a solution of n-BuLi (78 ml, 2.1 M) in hexane. After 15 min. CuBr·SMe₂ (32 g) was added in 3 portions. The reaction mixture was stirred at −78° C. until CuBr·SMe₂ was dissolved (approx. 1 hr.), then benzoyl chloride (20 mL) was added dropwise. The cooling bath was removed and the reaction mixture was stirred at room temperature over night and was quenched with a saturated NH₄Cl solution. The organic phage was diluted with Et₂O, washed with H₂O (3×), brine, dried (MgSO₄) and evaporated to afford the title compound which was used as such for the next step.

Step 2: 2-Benzoyl-5-benzyloxybenzaldehyde

A solution of crude ketone from Step 1 in acetone (250 mL) and HCl 10% (25 mL) was stirred for 6 hours, diluted with Et₂O, washed with a saturated NH₄Cl solution, H20 (3×), brine and dried (MgSO₄). After evaporation of the solvent, the residue was saturated with hexane and filtered to afford the title compound as pale yellow solid.

Step 3:
7-Benzyloxy-4-phenylnaphthalene-2,3-dicarboxylic N-phenylimide

A solution of the keto aldehyde from Step 2 (27.9 g), N-phenyl maleimide (23 g) and triethyl phosphite (24 mL) in benzene (500 mL) was heated at reflux for 3 hours then stirred at room temperature overnight. The reaction mixture was filtered and the solid washed with Et₂O to give the title compound as a pale yellow solid.

Step 4:
7-Benzyloxy-4-phenylnaphthalene-2,3-dicarboxylic acid

A solution of the imide from Step-3 (5.3 g) in triglyme (30 mL) and NAOH (10N, 20 mL) was stirred at 120° C. for 48 hours. The reaction mixture was cooled, extracted with H₂O (2×), and the water phase acidified to pH 3 with conc. HCl, and filtered. The solid residue was dissolved in CHCl₃ and washed with H₂O, brine, dried (MgSO₄) and evaporated to afford the title compound which was used as such for the next step.

Step 5:
7-Benzyloxy-4-phenylnaphthalene-2,3-carboxylic anhydride

To a solution of the crude acid from Step 4 in THF (20 mL) at 0° C. was added trifluoroacetic anhydride (TFAA) (5 mL) dropwise. The reaction mixture was stirred at 0° C. for 1 hour then at room temperature overnight. After evaporation of the solution, the residue was triturated with Et₂O and filtered to afford the title compound as a white solid.

Use of the title product is described in Method B, Step 3 and Method A, Step 5.

Method E

Step 1: Benzaldehyde phenyl dithioacetal

To a solution of benzaldehyde (31.8 g) and thiophenol (69.2 g) in isopropyl acetate (300 mL), cooled in an ice-water bath, there was slowly added BF₃·Et2O (42.6 9). The resulting mixture was stirred in the cold for an additional hour. There was slowly added 10% aqueous K₂CO₃ (200 mL) and the phases were separated. The aqueous phase was extracted with EtOAc and the combined organic layers were washed with 10% aq. K₂CO₃, then with H₂O (3×), dried and evaporated down to an oil which solidified. This solid was stirred in pentane (250 mL) at r.t. for 5 hr. and filtered to afford the desired dithioacetal.

Step 2:
3-[α,α-bis(Phenylthio)benzyl]-2-(3-benzyloxy-α-hydroxybenzyl)butyrolactone To a solution of the dithioacetal from Step 1 (23.5 g) in THF (250 mL), at −70° C. there was slowly added 2.1M n-BuLi in hexanes (37 mL). The resulting yellow suspension was stirred for a further 20 min at. −70° C., then there was added dropwise 2-(5H)furanone (Omega Inc., 7.64 g) and, 30 min later, a solution of 3-benzyloxybenzaldehyde (Aldrich, 16.5 g) in THF (75 mL). The mixture was stirred a further hour at −70° C., then there was slowly added glacial HOAC (9.0 g). The mixture was allowed to warm up to r.t., diluted with Et₂O (300 mL), washed with brine (4×), dried and evaporated. The residue was used as such in the next step.

Step 3:
7-Hydroxy-3-hydroxymethyl-4-phenyl-2-naphthoic acid, lactone form

The crude product from Step 2 was dissolved in thioanisole (75 mL). There was added TFA (190 mL) and the mixture was heated to 60° C. for 1 hr. After cooling, the TFA was evaporated, the residue was diluted with Et₂O (200 mL), and after 20 min, the insoluble solid was filtered to afford the desired title compound.

Lactone 2:
7-hydroxy-3-hydroxymethyl-4-(4-fluorophenyl)-2-naphthoic acid, lactone form

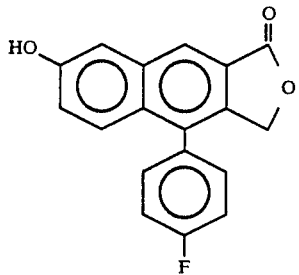

Following the procedures described in Lactone 1, Method A, Steps 3-5, but substituting 3-(4-fluorophenyl)-2-propyn-1-ol for 3-phenyl-2-propyn-1-ol, the title product was obtained as a solid.

Lactone 3:
7-Hydroxy-3-hydroxymethyl-4-(4-chlorophenyl)-2-naphthoic acid, lactone form Following the procedure described in Lactone 1, Method B, Steps 1-3, followed by Method A, Step 5, but substituting 4-chlorobenzaldehyde for benzaldehyde, the title compound was obtained as a solid.

Lactone 4.,
7-Hydroxy-3-hydroxymethyl-4-(4-methoxyphenyl)-2-naphthoic acid, lactone form Following the procedure described in Lactone 1, Method B, Steps 1-3, and followed by Method A, Step 5, but substituting 4-methoxybenzaldehyde for benzaldehyde, the title compound was obtained as a solid.

Lactone 5:
7-Hydroxy-3-hydroxymethyl-4-(2-fluorophenyl)-2-naphthoic acid, lactone form Following the procedure described in Lactone 1, Method B, Steps 1-3, and followed by Method A, Step 5, but substituting 2-fluorobenzaldehyde for benzaldehyde, the title product was obtained as a white solid.

Lactone 6:
7-Hydroxy-1-hydroxymethyl-4-(2-chlorophenyl)-2-naphthoic acid, lactone form Following the procedure described in Lactone 1, Method B, Steps 1-3, and followed by Method A, Step 5, but substituting 2-chlorobenzaldehyde for benzaldehyde, the title product was obtained as a white solid.

Lactone 7:
7-Hydroxy-3-hydroxymethyl-4-(3-methoxyphenyl)-2-naphthoic acid, lactone form Following the procedure described in Lactone 1, Method E, but substituting m-anisaldehyde for benzaldehyde, the title compound was obtained as a white solid.

EXAMPLES

The invention is further defined by reference to the following examples, which are intended to be illustrative and not limiting. All temperatures are in degrees Celsius.

EXAMPLE 1

3-Hydroxymethyl-4-phenyl-7-{3-[4-(4-methoxy)tetrahydropyranylbenzyloxy}-2-naphthoic acid, sodium salt

Step 1:
3-Hydroxymethyl-4-phenyl-7-{3-[4-(4-methoxy)tetrahydropyranyl]benzyloxy}-2-naphthoic acid, lactone form A mixture of 3-[4-(4-methoxy)tetrahydropyranyl]-benzyl bromide, (Halide 1), (1.04 g), 7-hydroxy-3-hydroxymethyl-4-phenyl-2-naphthoic acid lactone form (Lactone 1) (0.60 g), and potassium carbonate (0.78 g) in DMF (15 mL) was stirred at room temperature. After 17 hours, water was added and the aqueous phase was extracted with EtOAc. The combined organic phases were washed with 1N NaOH, water and brine before being dried (MgSO₄) and evaporated. The resulting solid was crystallized in EtOAc to afford the title compound as a pale yellow solid, m.p. 191°-192° C.

Step 2:
3-Hydroxymethyl-4-phenyl-7-{3-[4-(4-methoxy)tetrahydropyranyl]benzyloxy}-2-naphthoic acid, sodium salt A suspension of the lactone from Step 1 (0.50 g) in absolute ethanol (15 mL) was treated with 1N aqueous NaOH (1.2 mL) and refluxed for 21 hours. The resulting yellow solution was evaporated to dryness and gave the title salt as a yellow solid.

¹H NMR (250 MHz, DMSO-d₆): δ1.92 (m, 4H), 2.86 (s, 3H), 3.69 (m, 4H) 4.18 (d, 2H), 5.23 (s, 2H), 7.0-7.6 (m, 12 H), 7.82 (t, 1H), 8.07 (s, 1H).

EXAMPLE 2

3-Hydroxymethyl-4-phenyl-7-{3-[4-(4-methoxy)tetrahydropyranyl]phenoxymethyl}-2-naphthoic acid, sodium salt

Step 1:
3-Hydroxymethyl-4-phenyl-7-trifluoromethanesulfonyloxy-2-naphthoic acid, lactone form To a solution of Lactone 1 (141 mg) in $CH_2Cl_2$ (25 mL) and pyridine (400 μl) at −78° C. was added trifluoromethanesulfonic anhydride (150 μL) dropwise. The reaction mixture was stirred at room temperature for 30 min. diluted with $Et_2O$, quenched with a saturated $NH_4Cl$ solution, washed successively with HCl (10%, 2×), $H_2O$, brine and dried ($MgSO_4$). Purification by flash chromatography (hexane/EtOAc, 95% to 85%) gave the title compound.

Step 2:
7-Carbomethoxy-3-hydroxymethyl-4-phenyl-2-naphthoic acid, lactone form To a solution fo the triflate ester from Step 1 (160 mg) in DMSO (5 mL) was added. MEOH (3 mL, $Et_3N$ (110 KL), 1,1-bis(diphenylphosphino)ferrocene (50 mg) and Pd(OAc)$_2$ (10 mg). The reaction mixture was saturated with carbon monoxide (bubbling for 10 min) then heated at 75° C. under a CO atmosphere for 15 min. The reaction was cooled, diluted with $Et_2O$, washed with saturated $NH_4Cl$ solution, $H_2O$, brine and dried ($MgSO_4$). Evaporation and purification of the residue by flash chromatography (hexane/EtOAc/CHCl$_3$ 75:15:10) afforded the title compound as a pale yellow solid.

Step 3:
7-Carboxy-3-hydroxymethyl-4-phenyl-2-naphthoic acid, lactone form

To a solution of the lactone from Step 2 (110 mg) in THF/$H_2O$ (4:1, 10 mL) was added LiOH·$H_2O$ (50 mg). After 30 min., the reaction mixture was acidified to pH 2-3, and the water phase saturated with NaCl. The organic phase was decanted, dried ($MgSO_4$) and evaporated. The residue was purified by flash chromatography (CHCl$_3$/MeOH, 85:15) to afford the title compound.

Step 4. 3,7-Dihydroxymethyl-4-phenyl-2-naphthoic acid, lactone form

To a solution of the acid from Step 3 (94 mg) in THF(10 mL) at −70° C. was added $Et_3N$ (65 μL), then isopropyl chloroformate (48 μL). After 20 min., $NaBH_4$ (25 mg) in $H_2O$ (2 mL) was added and the reaction mixture was stirred at room temperature for 30 min. The reaction was diluted with EtOAc and saturated $NH_4Cl$ solution, washed with $H_2O$, brine and dried ($MgSO_4$). After evaporation, the residue was purified by flash chromatography (CHCl$_3$/MeOH, 99:1 to 97:3) to give the title compound.

Step 5:
7-Bromomethyl-3-hydroxymethyl-4-phenyl-2-naphthoic acid, lactone form To a solution of the alcohol from Step 4 (76 mg) in $CH_2Cl_2$ (10 mL) at 0° C. was added Ph$_3$P (76 mg), imidazole (20 mg) and CBr$_4$ (90 mg). The reaction mixture was stirred 30 min. at 0° C. then diluted with $H_2O$, brine and dried ($MgSO_4$). After evaporation, the residue was purified by flash chromatography (hexane/EtOAc, 85:15) to give the title compound.

Step 6:
3-Hydroxymethyl-4-phenyl-7-{3-[4-(4-methoxy)tetrahydropyranyl]phenoxymethyl}-2-naphthoic acid, lactone form Following the procedure described in Example 1 but substituting 3-[4-(4-methoxy)tetrahydropyranyl]phenol (EP-A-351,194) for 7-hydroxy-3-hydroxymethyl- 4-phenyl-2-naphthoic acid, lactone form, and substituting 7-bromomethyl-3-hydroxymethyl-4-phenyl-2-naphthoic acid, lactone form, from Step 5 for 3-[4-(4-methoxy)tetrahydropyranyl]benzyl bromide, the title product was obtained as a cream colored solid, m.p. 165°-166° C.

Step 7:
3-Hydroxymethyl-4-phenyl-7-{3-[4-(4-methoxy)tetrahydropyranyl]phenoxymethyl}-2-naphthoic acid, sodium salt Following the procedure described in Example 1, Step 2, but substituting the lactone from Step 6 for 3-hydroxymethyl-4-phenyl-7-{3-[4-(4-methoxy)tetrahydropyranyl]benzyloxy}-2-naphthoic acid, lactone form, the title product is obtained.

EXAMPLE 3

3-Hydroxymethyl-4-(4-fluorophenyl)-7-{3-[4-(4-methoxy)tetrahydropyranyl]benzyloxy}-2-naphthoic acid, sodium salt

Step 1:
3-Hydroxymethyl-4-(4-fluorophenyl)-7-{3-[4-(4-methoxy)tetrahydropyranyl]benzyloxy}-2-naphthoic acid, lactone form Following the procedure described in Example 1 but substituting 7-hydroxy-3-hydroxymethyl-4-(4-fluorophenyl)-2-naphthoic acid, lactone form, (Lactone 2), for 7-hydroxy-3-hydroxymethyl-4-phenyl-2-naphthoic acid, lactone form, the title compound was obtained as a white solid, m.p. 140°-141° C.

Step 2:
3-Hydroxymethyl-4-(4-fluorophenyl)-7-{3-[4-(4-methoxy)tetrahydropyranyl]benzyloxy}-2-naphthoic acid, sodium salt Following the procedure described in Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product is obtained.

EXAMPLE 4

3-Hydroxymethyl-4-phenyl-7-{3-[4-(4-hydroxy)tetrahydropyranyl]benzyloxyl-2-naphthoic acid, sodium salt

Step 1:
3-Hydroxymethyl-4-phenyl-7-{3-[4-(4-hydroxy)tetrahydropyranyl]benzyloxy}-2-naphthoic acid, lactone form Following the procedure described in Example 1 but substituting 3-[4-(4-hydroxy)tetrahydropyranyl]-benzyl bromide (Halide 2) for 3-[4-(4-methoxy)tetrahydropyranyl]benzyl bromide, the title product was obtained as a white solid, m.p. 191°-192° C.

Step 2:
3-Hydroxymethyl-4-phenyl-7-{3-[4-(4-hydroxy)tetrahydropyranyl]benzyloxy}-2-naphthoic acid, sodium salt Following the procedure of Example 1, Step 2, but but substituting the lactone from Step 1 for 3-hydroxymethyl-4-phenyl-7-{3-[4-methoxy)tetrahydropyranyl]benzyloxy}- 2-naphthoic acid, lactone form, the title product was obtained as a yellow solid. $^1$H NMR(250 MHz, DMSO-$d_6$): δ1.56 (m, 2H), 1.98 (m, 2H), 3.75 (m, 4H) 4.17 (d, 2H), 5.09 (s, 1H), 5.21 (s, 2H) 7.0–7.6 (m, 11 H), 7.65 (s, 1H), 7.95 (br s, 1H), 8.05 (s, 1H).

EXAMPLE 5

3-Hydroxymethyl-4-phenyl-7-{3-[4-(4-ethoxy)-tetrahydropyranyl]benzyloxy}-2-naphthoic acid, sodium salt Step 1:
3-Hydroxymethyl-4-phenyl-7-{3-[4-(4-ethoxy)tetrahydropyranyl]benzyloxy}-2-naphthoic acid, lactone form Following the procedure described in Example 1 but substituting 3-[4-(4-ethoxy)tetrahydropyranyl]benzyl bromide (Halide 3) for 3-[4-(4-methoxy)tetrahydropyranyl]benzyl bromide, the title compound was obtained as a white solid, m.p. 153°–155° C.

Step 2: 3-Hydroxymethyl-4-phenyl-7-{ 3-[4-(4-ethoxy)tetrahydropyranyl]benzyloxy}-2-naphthoic acid, sodium-salt Following the procedure of Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product was obtained as a yellow solid. $^1$H-NMR (250 MHz, DMSO-$d_6$): δ1.02 (t, 3H), 1.90 (m, 4H), 2.99 (q, 2H), 3.70 (m, 4H), 4.18 (d, 2H), 5.24 (s, 2H), 7.0–7.6 (m, 12H), 7.82 (t, 1H), 8.06 (s, 1H).

EXAMPLE 6

5-Hydroxymethyl-4-phenyl-7-{3-(1-methoxycyclohexyl)benzyloxy}-2-naphthoic acid, sodium salt Step 1:
3-Hydroxymethyl-4-phenyl-7-13-(1-methoxycyclohexyl)benzyloxy}-2-naphthoic acid, lactone form Following the procedure described in Example 1 but substituting 3-(1-methoxycyclohexyl)benzyl bromide (Halide 4) for 3-[4-(4-methoxy)tetrahydropyranyl]benzyl bromide, the title compound was obtained as a white solid, m.p. 174°–176° C.

Step 2:
3-Hydroxymethyl-4-phenyl-7-{3-(1-methoxycyclohexyl)benzyloxy}-2-naphthoic acid, sodium salt Following the procedure described in Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product is obtained.

EXAMPLE 7

3-Hydroxymethyl-4-phenyl-7-{3-(N-morpholino)benzyloxy}-2-naphthoic acid, sodium salt Step 1:
3-Hydroxymethyl-4-phenyl-7-[3-(N-morpholino)benzyloxy]-2-naphthoic acid, lactone form Following the procedure described in Example 1 but substituting 3-(N-morpholino)benzyl chloride (Halide 5) for 3-[4-(4-methoxy)tetrahydropyranyl]benzyl bromide, the title product was obtained as a white solid, m.p. 194°–196° C.

Step 2:
3-Hydroxymethyl-4-phenyl-7-{3-(N-morpholino)benzyloxy}-2-naphthoic acid, sodium salt Following the procedure described in Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product is obtained.

EXAMPLE 8

3-Hydroxymethyl-4-phenyl-7-{3-(N-oxomorpholino)-benzyloxy}-2-naphthoic acid, sodium salt Step 1:
3-Hydroxymethyl-4-phenyl-7-{3-(N-oxomorpholino)-benzyloxy}-2-naphthoic acid, lactone form To a solution of 3-hydroxymethyl-4-phenyl-7-[3-(N-morpholino)benzyloxy]-2-naphthoic acid, lactone form (from Example 7, Step 1) (40 mg; 0.08 mmol) in dichloromethane (5 mL) was added 85% meta-chloroperbenzoic acid (28 mg; 0.11 mmol). The mixture was stirred for one hour at room temperature and then excess calcium hydroxide added. After stirring for 15 minutes the mixture was filtered through celite and the filtrate concentrated. The residue was chromatographed using 10% methanol in dichloromethane to obtain the title compound, m.p. 199°–200° C.

Step 2:
3-Hydroxymethyl-4-phenyl-7-[3-(N-oxomorpholino)-benzyloxy]-2-naphthoic acid, sodium salt Following the procedure described in Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product is obtained.

EXAMPLE 9

3-Formyl-4-phenyl-7-{3-[4-(4-methoxy)tetrahydropyranyl)benzyloxy}-2-naphthoic acid, sodium salt Step 1:
3-Formyl-4-phenyl-7-{3-[4-(4-methoxy)tetrahydropyranyl)benzyloxy}-2-naphthoic acid, lactone form A suspension of 3-hydroxymethyl-4-phenyl-7-{3-[4-(4-methoxy)tetrahydropyranyl]benzyloxy}-2-naphthoic acid sodium salt (9 mg) from Example 1 in $CH_2Cl_2$ (0.5 mL) was treated with pyridinium chlorochromate (5 mg) at room temperature for 40 minutes. The mixture was then eluted through a short column of silica gel with 5% methanol in chloroform. Preparative thin layer chromatography of the residue gave the title compound as a colorless gum.

¹H NMR (250 MHz, CDCl₃): δ 2.00 (m, 4H), 2.99 (s, 3H), 3.85 (m, 4H), 5.25 (s, 2H), 6.63 (s, 1H), 7.25-7.55 (m, 12H), 7.69 (d, 1H) and 8.33 (s, 1H).

Step 2:
3-Formyl-4-phenyl-7-{3-[4-(4-methoxy)tetrahydropyranyl)benzyloxy}-2-naphthoic acid, sodium salt Following the procedure described in Example 1, Step 2, but substituting the lactone from Step 1 for 3-hydroxymethyl-4-phenyl-7-{3-[4-(4-methoxy)tetrahydropyranyl]benzyloxy}-2-naphthoic acid, lactone form, the title product is obtained.

EXAMPLE 11

3-Hydroxymethyl-4-phenyl-7-[3-[4-(2,4-dihydroxy)tetrahydropyranyl]benzyloxy]-2-naphthoic acid, sodium salt Step 1:
3-Hydroxymethyl-4-phenyl-7-[3-[4-(4-hydroxy-2-methoxy)tetrahydropyranyl]benzyloxy]-2-naphthoic acid, lactone form Following the procedure described in Example 1 but substituting 3-[4-(4-hydroxy-2-methoxy)tetrahydropyranyl]benzyl bromide (Halide 8) for 3-[4-(4-methoxy)tetrahydropyranyl]benzyl bromide, the title compound was obtained as a yellow gum.

Step 2:
3-Hydroxymethyl-4-phenyl-7-[3-[4-(2,4-dihydroxy)tetrahydropyranyl]benzyloxy]-2-naphthoic acid, lactone form To a solution of the methoxy alcohol (85 mg) from Step 1 in THF (1.5 mL) was added 10% aqueous HCl (1 mL) and the resulting solution was stirred at r.t. for 3 hr. The reaction mixture was basified with a solution of NaHCO₃ and extracted with EtOAc. The organic layer was washed with brine, dried over MgSO₄, and evaporated to dryness. The residue was purified by preparative TLC (silica gel; CHCl₃/EtOAc, 40:60) to afford the title product as a white solid.

¹H NMR (250 MHz, CDCl₃): δ 1.83 (m, 1H), 2.05 (m,2H), 2.31 (dt, 1H), 3.81 (m, 1H), 3.82 (s, 1H), 4.37 (d, 1H), 4.43 (dt, 1H), 5.22 (s, 2H), 5.24 (s, 2H), 5.41 (m, 1H), 7.29-7.59 (m, 10H), 7.67 (s, 1H), 7.73 (d, 1H) and 8.36 (s, 1H).

Step 3:
3-Hydroxymethyl-4-phenyl-7-[3-[4-(2,4-dihydroxy)tetrahydropyranyl]benzyloxy]-2-naphthoic acid, sodium salt Following the procedure described in Example 1, Step 2, but substituting the lactone from Step 2 for 3-hydroxymethyl-4-phenyl-7-[3-[4-(4-methoxy)tetrahydropyranyl]benzyloxy]-2-naphthoic acid, lactone form, the title product is obtained.

EXAMPLE 12

3-Formyl-4-phenyl-7-[3-[4-(4-hydroxy)tetrahydropyranyl]benzyloxy]-2-naphthoic acid, sodium salt Step 1:
3-Formyl-4-phenyl-7-[3-[4-(4-hydroxy)tetrahydropyranyl]benzyloxy]-2-naphthoic acid, lactone form Following the procedure described in Example 9, Steps 1-2, but substituting the lactone from Example 4 for the lactone from Example 1, the title compound was obtained as a white solid, m.p. 214°-218° C.

Step 2:
3-Formyl-4-phenyl-7-[3-[4-(4-hydroxy)tetrahydropyranyl]-benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 16

3-Hydroxymethyl-4-phenyl-7-[3-[4-(4α-hydroxy-2,6-dimethyl)tetrahydropyranyl]benzyloxy]-2-naphthoic acid, sodium salt Step 1:
3-Hydroxymethyl-4-phenyl-7-[3-[4-(4α-hydroxy-2,6-dimethyl)tetrahydropyranyl]benzyloxy]-2-naphthoic acid, lactone form Following the procedure described in Example 1 but substituting 3-[4-(4α-hydroxy-2,6-dimethyl)tetrahydropyranyl]benzyl bromide (Halide 7) for 3-[4-(4-methoxy)tetrahydropyranyl]benzyl bromide (Halide 1) and substituting Cs₂CO₃ for K₂CO₃, the title compound was obtained as a white solid.

¹H NMR (250 MHz, CDCl₃: δ 1.2 (d, 6H); 1.5-1.7 (m, 4H); 2.4 (broad s, 1H); 4.0 (m, 2H); 5.2-5.3 (2s, 4H); 7.2-7.6 (m, 11H); 7.75 (d, 1H); 8.4 (s, 1H).

Step 2:
3-Hydroxymethyl-4-phenyl-7-[3-[4-(4α-hydroxy-2,6-dimethyl)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product was obtained.

¹H NMR (250 MHz, DMSO-d₆): δ 1.1 (d, 6H); 1.4-1.7 (m, 4H); 3.8 (m, 2H); 4.2 (d, 2H); 5.0-5.1 (m, 1H); 5.2 (s, 2H); 7.1 (q, 1H); 7.2 (d, 1H); 7.3-7.7 (m, 8H); 7.9 (d, 1H); 8.0 (s, 1H); 8.5 (s, 1H).

EXAMPLE 17

3-Hydroxymethyl-4-phenyl-7-[3-[4-(4β-hydroxy-2,6-dimethyl)tetrahydropyranyl]benzyloxy]-2-naphthoic acid, sodium salt Step 1:
3-Hydroxymethyl-4-phenyl-7-[3-[4-(4β-hydroxy-2,6-dimethyl)tetrahydropyranyl]benzyloxy]-2-naphthoic acid, lactone form Following the procedure described in Example 1 but substituting 3-[4-(4β-hydroxy-2,6-dimethyl)tetrahydropyranyl]benzyl bromide (Halide 6) for 3-[4-(4-methoxy)tetrahydropyranyl]benzyl bromide (Halide 1) and substituting Cs₂CO₃ for K₂CO₃, the title compound was obtained as a white solid.

¹H NMR (250 MHz, CDCl₃: δ 1.2 (d, 6H); 1.65 (t, 2H); 1.9 (broad s, 1H); 2.4 (d, 2H); 3.4 (m, 2H); 5.25 (s, 4H); 7.2-7.6 (m, 11H); 7.75 (d, 1H); 8.4 (s, 1H).

Step 2:
3-Hydroxymethyl-4-phenyl-7-[3-[4-(4β-hydroxy-2,6-dimethyl)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 18

3-Hydroxymethyl-4-(4-chlorophenyl)-7-[3-[4-(4-hydroxy)tetrahydropyranyl]benzyloxy]-2-naphthoic acid, sodium salt Step 1:

3-Hydroxymethyl-4-(4-chlorophenyl)-7-[3-[4-(4-hydroxy)tetrahydropyranyl]benzyloxy]-2-naphthoic acid, lactone form A mixture of Lactone 3 (450 mg, 1.45 mmol), Halide 2 (434 mg, 1.6 mmol) and $Cs_2CO_3$ (520 mg, 1.6 mmol) in DMF (10 mL) was stirred at r.t. for two hr. The mixture was diluted with $H_2O$ and extracted twice with EtOAc. The extracts were washed twice with brine, dried, and evaporated. The residue was chromatographed on silica gel, eluting with a 60:40 mixture of hexane and EtOAc, to afford the title compound. This was stirred at r.t. in a small volume of $Et_2O$ for 1 hr and filtered to afford the purified desired product; m.p. 125°–127° C.

Step 2:

3-Hydroxymethyl-4-(4-chlorophenyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]- 2-naphthoic acid, lactone form, the title product is obtained.

EXAMPLE 19

3-Hydroxymethyl-4-(4-methoxyphenyl)-7-[3-[4-hydroxy)tetrahydropyranyl]benzyloxy]-2-naphthoic acid, sodium salt Step 1:

3-Hydroxymethyl-4-(4-methoxyphenyl)-7-[3-[4-hydroxy)tetrahydropyranyl]benzyloxy]-2-naphthoic acid, lactone form Following the procedure described in Example 18, but substituting 7-hydroxy-3-hydroxymethyl-4-(4-methoxyphenyl)-2-naphthoic acid, lactone form (Lactone 4) for 7-hydroxy-3-hydroxymethyl-4-(4-chlorophenyl)-2-naphthoic acid, lactone form (Lactone 3), the title compound was obtained as a solid; m.p. 220°–225° C.

Step 2:

3-Hydroxymethyl-4-(4-methoxyphenyl)-7-[3-[4-hydroxy)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 20

3-Hydroxymethyl-4-phenyl-7-[3-[4-(4α-methoxy-2,6-dimethyl)tetrahydropyranyl]benzyloxy]-2-naphthoic acid, sodium salt Step 1:

3-Hydroxymethyl-4-phenyl-7-[3-[4-(4α-methoxy-2,6-dimethyl)tetrahydropyranyl]benzyloxy]-2-naphthoic acid, lactone form A mixture of 3-hydroxymethyl-4-phenyl-7-[3-[4-(4α-hydroxy-2,6-dimethyl)tetrahydropyranyl]benzyloxy]-2-naphthoic acid lactone form (from Example 17) (50 mg) in DMF (1 mL) was stirred at r.t. with excess of NaH and MeI. A solution of $NH_4Cl$ was added and the reaction mixture was extracted with EtOAc and the combined organic phase was dried and evaporated. Flash column of the residue with 30% EtOAc in hexane afforded the title compound as a solid; m.p. 195° C.

Step 2:

3-Hydroxymethyl-4-phenyl-7-[3-[4-(4α-methoxy-2,6-dimethyl)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 21

3-Hydroxymethyl-4-phenyl-7-[3-[4-(4-hydroxy)tetrahydrothiopyranyl]benzyloxy]-2-naphthoic acid, sodium salt Step 1:

3-Hydroxymethyl-4-phenyl-7-[3-[4-(4-hydroxy)tetrahydrothiopyranyl]benzyloxy]-2-naphthoic acid, lactone form Following the procedure described in Example 1, but substituting 3-[4-(hydroxy)tetrahydrothiopyranyl]benzyl chloride (Halide 12) for 3-[4-(4-methoxy)tetrahydropyranyl]benzyl bromide (Halide 1) and substituting $Cs_2CO_3$ for $K_2CO_3$, the title compound was obtained as a white solid; m.p. 203°–205° C.

Step 2:

3-Hydroxymethyl-4-phenyl-7-[3-[4-(4-hydroxy)tetrahydrothiopyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product was obtained.

$^1$H NMR (250 MHz, DMSO-$d_6$): δ 2.1–1.8 (m, 4H); 2.4 (d, 2H); 3.1 (dd, 2H); 4.2 (d, 2H); 5.0–5.2 (m, 1H); 5.2 (s, 2H); 7.1 (q, 1H); 7.2 (d, 1H); 7.3–7.8 (m, 8H); 7.9 (s, 1H); 8.2 (s, 1H); 8.5 (s, 1H).

EXAMPLE 22

3-Hydroxymethyl-4-phenyl-7-[3-[4-(4-hydroxy-S-oxo)-tetrahydrothiopyranyl]benzyloxy]-2-naphthoic acid, sodium salt

Step 1:

3-Hydroxymethyl-4-phenyl-7-[3-[4-(4-hydroxy-S-oxo)-tetrahydrothiopyranyl]benzyloxy]-2-naphthoic acid, lactone form To a solution at −78° C. of 3-hydroxymethyl-4-phenyl-7-[3-[4-(4-hydroxy)tetrahydrothiopyranyl]benzyloxy-2-naphthoic acid, lactone form (from Example 21) (50 mg; 0.1 mmol) in CH$_2$Cl$_2$ (1 mL) and THF (1 mL) was added 85% meta-chloroperbenzoic acid (21 mg; 0.12 mmol). The mixture was stirred for one hr. at −78° C. and then filtered through celite and the filtrate concentrated. The residue was chromatographed using 5% MEOH in CHCl$_3$ to obtain the title compound as a foam.

$^1$H NMR (250 MHz, CDCl$_3$): δ 1.8 (d, 2H); 2.7–3.4 (m, 7H); 5.2–5.3 (2s, 4H); 7.2–7.8 (m, 12H); 8.3 (s, 1H).

Step 2:

3-Hydroxymethyl-4-phenyl-7-[3-[4-(4-hydroxy-S-oxo)-tetrahydrothiopyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 23

3-Hydroxymethyl-4-phenyl-7-[3-[4-(4-hydroxy-S,S-dioxo)tetrahydrothiopyranyl]benzyloxy]-2-naphthoic acid, sodium salt

Step 1:

3-Hydroxymethyl-4-phenyl-7-[3-[4-(4-hydroxy-S,S-dioxo)tetrahydrothiopyranyl]benzyloxy]-2-naphthoic acid, lactone form Using 3.0 eq. of meta-chloroperbenzoic acid, the procedure described in Example 22 was followed. Aqueous work-up was done using EtOAc/NH$_4$OAc extraction (3×). The combined organic layer was dried and evaporated to give, after flash chromatography, the title compound as a solid; m.p. 247°–249° C.

Step 2:

3-Hydroxymethyl-4-phenyl-7-[3-[4-(4-hydroxy-S,S-dioxo)tetrahydrothiopyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 24

3-Hydroxymethyl-4-phenyl-7-[3-[4-(4-hydroxy-2α-methoxytetrahydropyranyl]benzyloxy]-2-naphthoic acid, sodium salt

Step 1:

3-Hydroxymethyl-4-phenyl-7-[3-[4-(4-hydroxy-2α-methoxytetrahydropyranyl]benzyloxy]-2-naphthoic acid, lactone form, and
3-hydroxymethyl-4-phenyl-7-[3-[4-(4-hydroxy-2β-methoxytetrahydropyranyl]benzyloxy]-2-naphthoic acid, lactone form To a solution of the diol (77 mg) from Example 11 in MEOH (3 mL) and THF (3 mL) was added p-TSA (2 mg) and the resulting solution was stirred at r.t. 21 hr. The solvents were then evaporated under reduced pressure and the residue was purified by flash chromatography (silica gel; CHCl$_3$/EtOAc, 75:25 to 60:40) to afford first the α-glycoside as a white solid, (m.p. 179°–180° C.) followed by the β-glycoside as a white solid.

$^1$H NMR (250 MHz, CDCl$_3$): δ 1.69 (m, 1H), 1.82 (s, 1H), 1.94–2.13 (m, 3H), 3.54 (s,3H), 4.00–4.04 (m, 2H), 4.79 (dd, 1H), 5.20 (s, 2H), 5.23 (s, 2H), 7.28–7.64 (m, 11H), 7.72 (d, 1H), 8.35 (s, 1H).

Step 2:

3-Hydroxymethyl-4-phenyl-7-[3-[4-(4-hydroxy-2α-methoxytetrahydropyranyl]benzyloxy]-2-naphthoic acid, sodium salt Following the procedure described in Example 1, Step 2, but substituting the α-glycoside lactone from Step 1 for 3-hydroxymethyl-4-phenyl-7-[3-[4-(4-methoxy)tetrahydropyranyl]benzyloxy]-2-naphthoic acid, lactone form, the title product was obtained.

$^1$H NMR (250 MHz, DMSO-d$_6$): δ 1.56 (d, 1H); 1.77 (d, 1H); 2.12 (m, 2H); 3.30 (s, 3H); 3.53 (m, 1H); 4.06 (td, 1H); 4.17 (s, 2H); 4.73 (s, 1H); 5.20 (s, 2H); 7.03–7.55 (m, 11H); 7.65 (s, 1H); 8.07 (s, 1H).

EXAMPLE 25

3-Hydroxymethyl-4-phenyl-7-[3-[4-(4-hydroxy-2β-methoxytetrahydropyranyl]benzyloxy]-2-naphthoic acid, sodium salt Following the procedure described in Example 1, Step 2, but substituting the β-glycoside lactone from Example 24, Step 1, for 3-hydroxymethyl-4-phenyl-7-[3-[4-(4-methoxy)tetrahydropyranyl]benzyloxy]-2-naphthoic acid, lactone form, the title product is obtained.

EXAMPLE 26

3-Hydroxymethyl-4-phenyl-7-[3-[4-(4-methyl)tetrahydropyranyl]benzyloxy]-2-naphthoic acid, sodium salt

Step 1:

3-Hydroxymethyl-4-phenyl-7-[3-[4-(4-methyl)tetrahydropyranyl]benzyloxy]-2-naphthoic acid, lactone form Following the procedure described in Example 1 but substituting 3-[4-(4-methyl)tetrahydropyranyl]benzyl bromide (Halide 9) for 3-[4-(4-methoxy)tetrahydropyranyl]benzyl bromide, the title lactone was obtained as a white solid.

$^1$H NMR (250 MHz, CDCl$_3$): δ 1.32 (s, 3H), 1.72–1.85 (m, 2H), 2.08–2.20 (m, 2H), 3.63–3.85 (m, 4H), 5.23 (s, 2H), 5.26 (s, 2H), 7.30–7.60 (m, 11H), 7.74 (d, 1H), 8.39 (s, 1H).

Step 2:
3-Hydroxymethyl-4-phenyl-7-[3-[4-(4-methyl)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 27
3-(1-Hydroxyethyl)-[3-[4-hydroxy)tetrahydropyranyl]benzyloxy]-4-phenyl-2-naphthoic acid, sodium salt

Step 1:
7-benzyloxy-2,3-bis(hydroxymethyl)-4-phenylnaphthalene

To a suspension of LAH (3 g) in THF (50 mL) at 0° C., was added the anhydride from Lactone 1, Method B, Step 2 (6 g) in small portions. The resulting reaction mixture was stirred at r.t. 2 hr. then heated to reflux for 55 hr. After cooling to 0° C., an aqueous solution of 6N HCl was added dropwise until the aluminum salts dissolved. The mixture was diluted with EtOAc, washed with $H_2O$ (3×), brine, dried over $MgSO_4$, and the solvent evaporated. The residue was swished in ether for 1 hr, then filtered to afford the title diol as a white solid.

Step 2:
7-Benzyloxy-2-(tert-butyldiphenylsilyloxymethyl)-3-hydrozymethyl-4-phenylnaphthalene To a solution of diol.(1.02 g) from Step 1 in DMF (15 mL) was added imidazole (410 mg) and t-BuPh$_2$SiCl (790 μL) at r.t. After 1 hr. the reaction mixture was diluted with Et$_2$O, washed with H$_2$O (3×), brine, dried over MgSO$_4$, and the solvent evaporated. The residue was purified by chromatography on silica gel using hexane/EtOAc 95:5 to give the title product.

Step 3:
7-Benzyloxy-2-(tert-butyldiphenylsilyloxymethyl)-3-formyl-4-phenylnaphthalene To a solution of alcohol (1.2 g) from Step 2 in CH$_2$Cl$_2$ (25 mL) was added molecular sieves powder (1 g, flame dried) and PCC (1 g). After 40 min, the reaction mixture was poured on a plug of SiO$_2$ (wet with Et$_2$O), and eluted with Et$_2$O. The solvent was evaporated to give the title product.

Step 4:
7-Benzyloxy-2-(tert-butyldiphenylsilyloxymethyl)-3-(1-hydroxyethyl)-4-phenylnaphthalene To a solution of aldehyde (1.1 g) from Step 3 in THF (15 mL) at −78° C., was added MeMgBr (1.4M PhMe-THF, 2.8 mL) dropwise. After 10 min, the bath was removed and the reaction mixture quenched with a saturated solution of NH$_4$Cl. The reaction was diluted with Et$_2$O, washed with saturated NH$_4$Cl solution, H$_2$O, brine, dried over MgSO$_4$, and the solvent evaporated to afford the title product as a foam.

Step 5:
3-(1-Acetoxyethyl)-7-benzyloxy-2(tert-butyldiphenylsilyloxymethyl)-4-phenylnaphthalene To a solution alcohol (300 mg) from Step 4 in Ac$_2$O (2 mL) was added pyridine (300 mL) and DMAP (2 mg). After 2 hr, the reaction mixture was diluted with Et$_2$O, washed with H$_2$O, a solution of CuSO$_4$, and the solvent evaporated to give the title product which was used as such for the next step.

Step 6:
3-(1-Acetoxyethyl)-7-benzyloxy-2-hydroxymethyl-4-phenylnaphthalene

To a solution of the crude ether from Step 5 in THF (10 mL) at 0° C. was added HOAC (4 drops) followed by n-Bu$_4$NF (1M, THF, 1.4 mL). The reaction mixture was stirred 2 hr. at 0° C. then quenched with a saturated solution of NH$_4$Cl and diluted with Et$_2$O. The organic phase was washed with H$_2$O, brine, dried over MgSO$_4$, and the solvent evaporated. The residue was purified by chromatography on silica gel using hexane/EtOAc, 7:3, to give the title product.

Step-7:
3-(1-Acetoxyethyl)-7-benzyloxy-4-phenyl-2-naphthoic acid

To a solution of alcohol (110 mg) from Step 6 in t-BuOH (6 mL) was added a KH$_2$PO$_4$ buffer solution (pH 7, 4 mL) and a solution of KMnO$_4$ (90 mg/2 mL H$_2$O). After 3 hr. at r.t., the reaction mixture was diluted with EtOAc and an aqueous solution of Na$_2$SO$_3$. The mixture was then acidified to pH 2, the organic phase was separated, washed with H$_2$O, brine, dried over MgSO$_4$ and evaporated to give the title product which was used as such for the next step.

Step 8:
7-Benzyloxy-3-(1-hydroxyethyl)-4-phenyl-2-naphthoic acid, lactone form To a solution of the crude acid (100 mg) from Step 7 in MEOH (3 mL) was added NaOMe (cat.). After 24 hr, the solvent was evaporated to dryness. The residue was dissolved in EtOAc (3 mL) and HCl 6N (2 drops). The reaction mixture was stirred 20 min, washed with H$_2$O (3×), brine, dried over MgSO$_4$, and the solvant evaporated to afford the title compound.

Step 9:
7-Hydroxy-3-(l-hydroxyethyl-4-phenyl-2-naphthoic acid, lactone form

To a solution of the lactone (90 mg) from Step 8 in EtOAc was added 10% Pd/C (11 mg) and the reaction mixture was stirred under H$_2$ for 24 hr. The solution was filtered and the solvent evaporated to afford the title product.

Step 10:
3-(1-Hydroxyethyl)-[3-[4-hydroxy)tetrahydropyranyl]benzyloxy]-4-phenyl-2-naphthoic acid, lactone form Following the procedure described in Example 1 but substituting 7-hydroxy-3-(2-hydroxyethyl)-4-phenyl-2-naphthoic acid, lactone form, for 7-hydroxy-3-hydroxymethyl-4-phenyl-2-naphthoic acid, lactone form, the title product was obtained as a glassy solid after purification by chromatography on silica gel using hexane/EtOAc/CH$_2$Cl$_2$ (7:3:5).

$^1$H NMR (250 MHz,CDCl$_3$): δ 1.15 (d, 3H), 1.7 (m, 2H), 2.2 (m, 2H), 3.9 (m, 4H), 5,25 (s, 2H), 5.7 (q, 1H), 7.27–7.7 (m, 12H), 8.35(s, 1H).

Step 11:
3-(1-Hydroxyethyl)-[3-[4-hydroxy)tetrahydropyranyl]benzyloxy]-4-phenyl-2-naphthoic acid, sodium salt Following the procedure described in Example 1, Step 2, but substituting the lactone from Step 10 for 3-hydroxymethyl-4-phenyl-7-[3-[4-(4-methoxy)tetrahydropyranyl]benzyloxy]-2-naphthoic acid, lactone form, the title product is obtained.

EXAMPLE 28

3-Hydroxymethyl-4-(4-fluorophenyl)-7-[3-[4-(4-hydroxy)tetrahydropyranyl]benzyloxy]-2-naphthoic acid, sodium salt

Step 1:
3-Hydroxymethyl-4-(4-fluorophenyl)-7-[3-[4-(4-hydroxy)tetrahydropyranyl]benzyloxy]-2-naphthoic acid, lactone form Following the procedure described in Example 18, but substituting 7-hydroxy-3-hydroxymethyl-4-(4-fluorophenyl)-2-naphthoic acid, lactone form (Lactone 2) for 7-hydroxy-3-hydroxymethyl-4-(4-chlorophenyl)-2-naphthoic acid, lactone form (Lactone 3), the title compound was obtained as a solid; m.p. 167°-169° C. (dec).

Step 2:
3-Hydroxymethyl-4-(4-fluorophenyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product was obtained.
$^1$H NMR (300 MHz, DMSO-d$_6$): δ 1.53 (d, 2H), 2.0 (m, 2H), 3.65-3.85 (m, 4H), 4.18 (s, 2H), 5.08 (s, 1H), 5.22 (s, 2H), 7.10 (m, 2H), 7.23-7.50 (m, 8H), 7.66 (s, 1H), 7.90 (broad s, 1H), 8.06 (s, 1H).

EXAMPLE 29

3-Hydroxymethyl-4-phenyl-7-[3-[4-(4-ethyl)tetrahydropyranyl]benzyloxy]-2-naphthoic acid, sodium salt

Step 1:
3-Hydroxymethyl-4-phenyl-7-[3-[4-(4-ethyl)tetrahydropyranyl]benzyloxy]-2-naphthoic acid, lactone form Following the procedure described in Example 1 but substituting 3-[4-(4-ethyl)tetrahydropyranyl]benzyl bromide (Halide 10) for 3-[4-(4-methoxy)tetrahydropyranyl]benzyl bromide, the title lactone was obtained as a white solid; m.p. 157°-159° C.

Step 2:
3-Hydroxymethyl-4-phenyl-7-[3-[4-(4-ethyl)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 30

3-Hydroxymethyl-4-(fluorophenyl)-7-[3-[4-(4-hydroxy)tetrahydropyranyl]benzyloxy]-2-naphthoic acid, sodium salt

Step 1:
3-Hydroxymethyl-4-(fluorophenyl)-7-[3-[4-(4-hydroxy)tetrahydropyranyl]benzyloxy]-2-naphthoic acid, lactone form Following the procedure described in Example 18, but substituting 7-hydroxy-3-hydroxymethyl-4-(2-fluorophenyl)-2-naphthoic acid, lactone form (Lactone 5) for 7-hydroxy-3-hydroxymethyl-4-(4-chlorophenyl)-2naphthoic acid, lactone form (Lactone 3), the title compound was obtained as a solid; m.p. 194°-196° C.

Step 2:
3-Hydroxymethyl-4-(fluorophenyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 31

3-Hydroxymethyl-4-(2-chlorophenyl)-7-[3-[4-(4-hydroxy)tetrahydropyranyl]benzyloxy]-2-naphthoic acid, sodium salt

Step 1:
3-Hydroxymethyl-4-(2-chlorophenyl)-7-[3-[4-(4-hydroxy)tetrahydropyranyl]benzyloxy]-2-naphthoic acid, lactone form Following the procedure described in Example 18, but substituting 7-hydroxy-3-hydroxymethyl-4-(2-chlorophenyl)-2-naphthoic acid, lactone form (Lactone 6) for 7-hydroxy-3-hydroxymethyl-4-(4-chlorophenyl)-2-naphthoic acid, lactone form (Lactone 3), the title compound was obtained as a solid; m.p. 198°-200° C. (dec).

Step 2:
3-Hydroxymethyl-4-(2-chlorophenyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 32

3-Hydroxymethyl-4-(3-methoxyphenyl)-7-[3-[4-(4-hydroxy)tetrahydropyranyl]benzyloxy]-2-naphthoic acid, sodium salt

Step 1:
3-Hydroxymethyl-4-(3-methoxyphenyl)-7-[3-[4-(4-hydroxy)tetrahydropyranyl]benzyloxy]-2-naphthoic acid, lactone form Following the procedure described in Example 18, but substituting 7-hydroxy-3-hydroxymethyl-4-(3-methoxyphenyl)-2-naphthoic acid, lactone form (Lactone 7) for 7-hydroxy-3-hydroxymethyl-4-(4-chlorophenyl)-2-naphthoic acid, lactone form (Lactone 3), the title compound was obtained as a solid; m.p. 182°-184° C. (dec).

Step 2:
3-Hydroxymethyl-4-(3-methoxyphenyl)-7-[3-[4-(4-hydroxy)tetrahydropyranyl]benzyloxy]-2-naphthoic acid, sodium salt Following the procedure described in Example 1, Step 2,-but substituting the lactone from Step 1 for 3-hydroxymethyl-4-phenyl-7-[3-[4-(4-methoxy)tetrahydropyranyl]benzyloxy]-2-naphthoic acid, lactone form, the title product was obtained.

$^1$H NMR (300 MHz, DMSO-d$_6$): δ 1.53 (d, 2H), 1.98 (m, 2H), 3.65–3.85 (m, 4H), 3.80 (s, 3H), 4.18 (d, 2H), 5.09 (broad s, 1H), 5.21 (s, 2H), 6.80 (m, 2H), 6.98–7.12 (m, 2H), 7.18 (d, 1H), 7.43–7.52 (m, 5H), 7.66 (s, 1H), 7.95 (t, 1H), 8.05 (s, 1H).

EXAMPLE 33

3-Hydroxymethyl-4-phenyl-7-[3-[4-(4-hydroxy-2α-isopropyloxy)tetrahydropyranyl]benzyloxy]-2-naphthoic acid, sodium salt

Step 1:

3-Hydroxymethyl-4-phenyl-7-[3-[4-(4-hydroxy-2α-isopropyloxy)tetrahydropyranyl]benzyloxy]-2-naphthoic acid, lactone form, and 3-Hydroxymethyl-4-phenyl-7-[3-[4-(4-hydroxy-2β-isopro-pyloxy)tetrahydropyranyl]benzyloxy]-2-naphthoic acid, lactone form Following the procedure described in Examples 24 and 25, but substituting i-PrOH for MEOH, afforded the title compounds as a mixture. The two compounds were separated by flash chromatography (silica gel; CHCl$_3$/EtOAc, 90:10 to 80:20), affording first the α- then the β-glycoside, both as white solids.

α-Glycoside $^1$H NMR (250 MHz, CDCl$_3$): δ 1.19 (d, 3E), 1.33 (d, 3H), 1.74 (d, 1H), 1.93 (d, 1H), 2.17 (dd, 1H), 2.29 (dd, 1H), 3.77 (dd, 1H), 4.04.(m, 1H), 4.25 (td, 1H), 5.10 (s, 1H), 5.18 (d, 1H), 5.23 (s, 2H), 5.25 (s, 2H), 7.30–7.75(m, 12H) 8.38 (s, 1H).

β-Glycoside $^1$H NMR (250 MHz, CDCl$_3$): δ 1.19 (d, 3H), 1.26 (d, 3H), 1.68 (d, 1H), 1.99–2.13 (m, 4H), 3.98–4.13 (m, 3H), 4.98 (dd, 1H), 5.20 (s, 2H), 5.24 (s, 2H), 7.28–7.75 (m, 12H), 8.36 (s, 1H).

Step 2:

3-Hydroxymethyl-4-phenyl-7-(3-[4-(4-hydroxy-2α-isopropyloxy)tetrahydropyranyl]benzyloxy]-2-naphthoic acid, sodium salt Following the procedure described in Example 1, Step 2, but substituting the α-glycoside lactone from Step 1, for 3-hydroxymethyl-4-phenyl-7-[3-[4-(4-methoxy)tetrahydropyranyl]benzyloxy]-2-naphthoic acid, lactone form, the title product is obtained.

EXAMPLE 34

3-Hydroxymethyl-4-phenyl-7-[3-[4-(4-hydroxy-2β-isopropyloxy)tetrahydropyranyl]benzyloxy]-2-naphthoic acid, sodium salt Following the procedure described in Example 1, Step 2, but substituting the β-glycoside lactone from Example 33, Step 1, for 3-hydroxymethyl-4-phenyl-7-[3-[4-(4-methoxy)tetrahydropyranyl]benzyloxy]-2-naphthoic acid, lactone form, the title product is obtained.

EXAMPLE 35

3-Hydroxymethyl-4-phenyl-7-[3-[3-(8-oxabicyclo[3,2,1]-oct-6-en-3α-ol)]benzyloxy]-2-naphthoic acid, sodium salt

Step 1:

3-Hydroxymethyl-4-phenyl-7-[3-[3-(8-oxabicyclo[3,2,-1]oct-6-en-3α-ol)]benzyloxy]-2-naphthoic acid, lactone form Following the procedure described in Example 1, but substituting Halide 13 for 3-[4-(4-methoxy)tetrahydropyranyl]benzyl bromide, the title lactone was obtained as a white solid.

$^1$H NMR (250 MHz, CDCl$_3$): δ 1.92 (d, 2H), 2.55 (dd, 2H), 3.10 (s, 1H), 4.94 (d, 2H), 5.22 (s, 2H), 5.26 (s, 2H), 6.62 (s, 2H), 7.29–7.60 (m, 10H), 7.65 (s, 1H), 7.72 (s, 1H), 8.39 (s, 1H).

Step 2:

3-Hydroxymethyl-4-phenyl-7-[3-[3-(8-oxabicyclo[3,2,-1]oct-6-en-3α-ol)]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 36

3-Hydroxymethyl-4-phenyl-7-[3-[3-(8-oxabicyclo[3.2.-1]octan-3α-ol)]benzyloxy]-2-naphthoic acid, sodium salt

Step 1:

3-Hydroxymethyl-4-phenyl-7-[3-[3-(8-oxabicyclo[3.2.-1]octan-3α-ol)]benzyloxy]-2-naphthoic acid, lactone form Following the procedure described in Example 1 but substituting Halide 14 for 3-[4-(4-methoxy)tetrahydropyranyl]benzyl bromide, the title compound was obtained as an off-white solid.

$^1$H NMR (250 MHz, CDCl$_3$): δ 1.81 (m, 2H), 1.98 (m, 3H), 2.40 (m, 4H), 4.52 (m, 2H), 5.18 (s, 2H), 5.23 (s, 2H), 7.27–7.74 (m, 12H), 8.35 (s, 1H).

Step 2:

3-Hydroxymethyl-4-phenyl-7-[3-[3-(8-oxabicyclo[3.2.-1]octan-3α-ol)]benzyloxy]-2-naphthoic acid, sodium salt Following the procedure described in Example 1, Step 2, but substituting the lactone from Step 1, for 3-hydroxymethyl-4-phenyl-7-[3-[4-(4-methoxy)tetrahydropyranyl]benzyloxy]-2-naphthoic acid, lactone form, the title product was obtained.

$^1$H NMR (250 HMz, DMSO-d$_6$): δ 1.75 (m, 4H); 2.10 (dd, 2H); 2.33 (d, 2H); 4.17 (d, 2H); 4.37 (broad s, 2H); 4.99 (s, 1H); 5.19 (s, 2H); 7.03–7.54 (m, 12H); 7.87 (t, 1H); 8.06 (s, 1H).

EXAMPLE 37

3-Hydroxymethyl-4-phenyl-7-[3-[4-(hydroxy)tetrahydropyranyl]-4-methoxybenzyloxy]-2-naphthoic acid, sodium salt

Step 1:
3-Hydroxymethyl-4-phenyl-7-[3-[4-(hydroxy)tetrahydropyranyl]-4-methoxybenzyloxy]-2-naphthoic acid, lactone form Following the procedure described in Example 18 but substituting 3-[4-(4-hydroxy)tetrahydropyranyl]-4-methoxybenzyl bromide (Halide 15) for 3-[4-(4-hydroxy)tetrahydropyranyl]benzyl bromide (Halide 2) and 7-hydroxy-3-hydroxymethyl-4-phenyl-2-naphthoic acid lactone form (Lactone 1) for 7-hydroxy-3-hydroxymethyl-4-(4-chlorophenyl)-2-naphthoic acid lactone form (Lactone 3), the title product was obtained as a white solid.

$^1$H NMR (250 MHz, CDCl$_3$): δ 1.95 (m, 2H); 2.2 (dt, 2H); 2.85 (m, 2H); 3.95 (s, 3H); 4.0 (m, 2H); 5.15 (s, 2H); 5.25 (s, 2H); 7.0 (d, 1H); 7.3 (dd, 1H); 7.4 (m, 5H); 7.55 (m, 3H); 7.75 (d, 1H); 8.4 (s, 1H).

Step 2:
3-Hydroxymethyl-4-phenyl-7-[3-[4-(hydroxy)tetrahydropyranyl]-4-methoxybenzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 38

3-(1-Hydroxy-1-methylethyl)-4-phenyl-7-[3-[4-(4-hydroxy)tetrahydropyranyl]benzyloxy]-1-naphthoic acid, sodium salt

Step 1:
3-Acetyl-7-benzyloxy-2-hydroxymethyl-4-phenylnaphthalene

To a heterogeneous solution of 500 mg of 7-benzyloxy-2-hydroxymethyl-4-phenyl-3-naphthoic acid, lactone form (minor isomer obtained from Lactone 1, Method B, Step 3) in THF at −78° C. was added MeLi (1M, Et$_2$O, 2 mL). The reaction mixture was warmed slowly until the solution became homogeneous then quenched with a saturated NH$_4$Cl solution. The organic phase was diluted with Et$_2$O, washed with H$_2$O, brine, dried over MgSO$_4$ and the solvent evaporated to afford the title compound used as such in the next step.

Step 2: 3-Acetyl-7-benzyloxy-4-phenyl-2-naphthoic acid

Following the procedure described in Example 27, Step 7, substituting 3-(2-acetoxyethyl)-7-benzyloxy-2-hydroxymethyl-4-phenylnaphthalene for 3-acetyl-7-benzyloxy-2-hydroxymethyl-4-phenylnaphthalene, the title product was obtained and used as such in the next step.

Step 3:
7-Benzyloxy-3-(1-hydroxy-1-methylethyl)-4-phenyl-2-naphthoic acid, lactone form To a solution of the acid (150 mg) from Step 2 in THF at −8° C. was added MeMgBr (1.4M, 0.8 mL) dropwise. After 2 hr, the reaction mixture was quenched with 10% HCl and diluted with Et$_2$O. After another 2 hr, the organic phase was extracted, washed with H$_2$O, brine, dried over MgSO$_4$, and the solvent evaporated. The residue was purified by chromatography on silica gel using hexane/EtOAC/CH$_2$Cl$_2$ (85:15:30) to give the title product.

Step 4:
7-Hydroxy-3-(1-hydroxy-1-methylethyl)-4-phenyl-2-naphthoic acid, lactone form Following the procedure described in Lactone 1, Method A, Step 5, but substituting 7-benzyloxy-3-(1-hydroxy-1-methylethyl)-4-phenyl-2-naphthoic acid, lactone form, for 7-benzyloxy-3-hydroxymethyl-4-phenyl-2-naphthoic acid, lactone form, the title product was obtained and used as such in the next step.

Step 5:
3-(1-Hydroxy-1-methylethyl)-4-phenyl-7-[3-[4-(4-hydroxy)tetrahydropyranyl]benzyloxy]-1-naphthoic acid, lactone form Following the procedure described in Example 1, but substituting 7-hydroxy-3-(l-hydroxy-1-methylethyl)-4-phenyl-2-naphthoic acid, lactone form, for 7-hydroxy-3-hydroxymethyl-4-phenyl-2-naphthoic acid, lactone form, the title product was obtained as a white foam. After purification on flash chromatography (hexane/EtOAc, 1:1), the title compound was obtained.

$^1$H NMR (250 MHz,CDCl$_3$): δ 1.49 (s, 6H), 1.7 (m, 2H), 2.22 (m, 2H), 3.93 (m, 4H), 5.23 (s, 2H), 7.21–7.58 (m, 11H), 7.67 (s, 1H), 8.35 (s, 1H).

Step 6:
3-(1-Hydroxy-1-methylethyl)-4-phenyl-7-[3-[4-(4-hydroxy)tetrahydropyranyl]benzyloxy]-1-naphthoic acid, sodium salt Following the procedure described in Example 1, Step 2, but substituting the lactone from Step 5 for 3-hydroxymethyl-4-phenyl-7-[3-[4-(4-methoxy)tetrahydropyranyl]benzyloxy]-2-naphthoic acid, lactone form, the title product is obtained.

EXAMPLE 39

3-Hydroxymethyl-7-[3-[4-(4-hydroxy)tetrahydropyranyl]benzyloxy]-1-methoxy-4-phenyl-2-naphthoic acid, sodium salt

Step 1:
3-[α,α-bis(Phenylthio)benzyl]-2-(3-benzyloxybenzoyl)-butyrolactone

To a solution of the crude alcohol (10.8 g) from Lactone 1, Method E, Step 2, in CH$_2$Cl$_2$ (150 mL) at 0° C. was added molecular sieves powder (flame dried, 10 g) followed by PCC (10.5 g) portion. The reaction mixture was stirred at r.t. for 1 hr then poured on a SiO$_2$ plug (prewashed with Et$_2$O), and eluted with Et$_2$O. The solvent was evaporated and the residue purified by flash chromatography on silica gel using hexane/EtOAc, 80:20, to give the title product.

Step 2:
2-[α-Acetoxy(3-benzyloxybenzylidene)]-3[α,α-bis(phenylthio)benzyl]butyrolactone To a solution of the ketone from Step 1 (1.91 g) in CH$_2$Cl$_2$ (20 mL) was added Ac$_2$O (1.5 mL), Et$_3$N (2.3 mL) and DMAP (40 mg). The reaction mixture was stirred at r.t. for 18 hr then diluted with Et$_2$O and a saturated solution of NH$_4$Cl. The organic phase was extracted, washed with H₂O, brine, dried over MgSO₄, and the solvent evaporated to afford the title product as a foam which was used as such in the next step.

Step 3:
1-Acetoxy-7-benzyloxy-3-hydroxymethyl-4-phenyl-2-naphthoic acid, lactone form To a solution of acetoxy derivative (1.8 g) from Step 2, in TFA (8 mL) and thioanisole (2 mL) was stirred at 0° C. for 2 hr. The reaction mixture was diluted with Et₂O, washed with H₂O (3×), pH 7 buffer solution, brine, dried over MgSO₄, and the solvent evaporated. The residue was purified by chromatography on silica gel using hexane/EtOAc/CH₂Cl₂ (85:15:50) to give the title product.

Step 4:
7-Benzyloxy-1-hydroxy-3-hydroxymethyl-4-phenyl-2-naphthoic acid, lactone form To a solution of the lactone (320 mg) from Step 3, in MEOH/THF (5:1, 12 mL) was added a solution of NaOMe in MEOH (2 drops). After 18 hr the reaction mixture was acidified to pH 4 and the solvent evaporated. The residue was triturated in Et₂O and filtered to afford the title product as a white solid.

Step 5:
7-Benzyloxy-1-(t-butyldiphenylsilyloxy)-3-hydroxymethyl-4-phenyl-2-naphthoic acid, lactone form To a solution of alcohol (160 mg) from Step 4, in CH₂Cl₂ (10 mL) was added imidazole (60 mg) and t-BuPh₂SiCl (150 µL). The reaction mixture was stirred overnight then diluted with Et₂O, washed with H₂O and brine, and dried over MgSO₄, and the solvent evaporated. The residue was triturated in hexane and filtered to afford the title product as a white solid.

Step 6:
1-(t-Butyldiphenylsilyloxy)-7-hydroxy-3-hydroxymethyl-4-phenyl-2-naphthoic acid, lactone form To a solution of the lactone (120 mg) from Step 5, in EtOAc/CH₂Cl₂ (4:1) was added Pd(OH)₂/C 20% (30 mg). The reaction mixture was stirred under H₂ (balloon) for 36 hr. then filtered and the solvent evaporated. The residue was triturated in Et₂O and filtered to afford the title product as a white solid.

Step 7:
1-(t-Butyldiphenylsilyloxy)-3-hydroxymethyl-7-[3-[4-(4-hydroxy)tetrahydropyranyl]benzyloxy]-4-phenyl-2-naphthoic acid, lactone form Following the procedure described in Example 7 but substituting 1-(t-butyldiphenylsilyloxy)-7-hydroxy-3-hydroxy methyl-4-phenyl-2-naphthoic acid, lactone form, from Step 6 for 7-hydroxy-3-hydroxymethyl-4-phenyl-2-naphthoic acid, lactone form, the title product was obtained after purification on flash chromatography (hexane/EtOAc/CH₂Cl₂, 85:15:40 to 65:35:40).

Step-8:
1-Hydroxy-3-hydroxymethyl-7-[3-[4-(4-hydroxy)tetrahydro-pyranyl]benzyloxy]-4-phenyl-2-naphthoic acid, lactone form To a solution of lactone (44 mg) from Step 7, in THF (5 mL) at 0° C. was added a n-Bu₄NF solution (1M, 85 µl). The reaction mixture was stirred at r.t. for 1 hr then diluted with Et₂O and H₂O. The organic phase was extracted, washed with H₂O, brine, dried over MgSO₄, and the solvent evaporated. The residue was triturated in Et₂O and filtered to afford the title product as a pale yellow solid.

Step 9:
3-Hydroxymethyl-7-[3-[4-(4-hydroxy)tetrahydropyranyl]benzyloxy]-1-methoxy-4-phenyl-2-naphthoic acid, lactone form To a solution of phenol (13 mg) from Step 8, in THF (2 mL) at 0° C. was added NaH (~1.5 mg) followed by MeI (10 µL). The reaction mixture was stirred at r.t. overnight then quenched with a pH 7 buffer solution and diluted with Et₂O. The organic phase was washed with H₂O, brine, dried over MgSO₄, and the solvent evaporated. The residue was purified by chromatography on silica gel using hexane/EtOAc/CH₂Cl₂ (7:3:5) to give the title product as a white foam.

¹H NMR (250 MHz, CDCl₃): δ 1.65 (m, 2H), 2.15 (m, 2H), 3.85 (s, 3H), 3.92 (m, 4H), 5.2 (s, 2H), 5.65 (s, 2H), 7.2 (dd, 1H), 7.32–7.63 (m, 10H), 7.7 (s, 1H).

Step 10:
3-Hydroxymethyl-7-[3-[4-(4-hydroxy)tetrahydropyranyl]benzyloxy]-1-methoxy-4-phenyl-2-naphthoic acid, sodium salt Following the procedure described in Example 1, Step 2, but substituting the lactone from Step 9 for 3-hydroxymethyl-4-phenyl-7-[3-[4-(4-methoxy)tetrahydropyranyl]benzyloxy]-2-naphthoic acid, lactone form, the title product is obtained.

EXAMPLE 40

3-Hydroxymethyl-4-phenyl-7-[3-[4-(4α-hydroxy-2,2,6,6-tetramethyl)tetrahydrothiopyranyl]benzyloxy]-2-naphthoic acid, sodium salt

Step 1:
3-Hydroxymethyl-4-phenyl-7-[3-[4-(4α-hydroxy-2,2,6,6-tetramethyl)tetrahydrothiopyranyl]benzyloxy]-2-naphthoic acid, lactone form Following the procedure described in Example 1, but substituting 3-[4-(4α-hydroxy-2,2,6,6-tetramethyl)tetrahydrothiopyranyl]benzyl chloride, (Halide 11) for 3-[4-(4-methoxy)tetrahydropyranyl]benzyl bromide, and substituting Cs₂CO₃ for K₂CO₃, the title compound was obtained as a white foam.

¹H NMR (250 MHz, CDCl₃): δ 1.3 (s, 6H); 1.7 (s, 6H); 2.0 (m, 5H); 5.2–5.3 (2s, 4H); 7.2–7.7 (m, 12H); 8.4 (s, 1H).

Step 2:
3-Hydroxymethyl-4-phenyl-7-[3-[4-(4α-hydroxy-2,2,6,6-tetramethyl)tetrahydrothiopyranyl]benzyloxy]-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

EXAMPLE 41

3-Hydroxymethyl-4-phenyl-7-[3-[4-(4-hydroxy-2-oxo)-tetrahydropyranyl]benzyloxy-2-naphthoic acid, sodium salt

Step 1:
3-Hydroxymethyl-4-phenyl-7-[3-[4-(4-hydroxy-2-oxo)-tetrahydropyranyl]benzyloxy-2-naphthoic acid, lactone form A mixture of the diol (152 mg) from Example 11 and $Ag_2CO_3$ on celite (1.60 g; prepared as described in Tetrahedron, 31, 171 (1975)) in benzene (25 mL) was refluxed for 4 hr. Filtration and evaporation of the filtrate followed by flash chromatography (silica gel; $CHCl_3/EtOAc$, 3:2) yielded the title compound as a white solid.

$^1H$ NMR (250 MHz, $CDCl_3$): δ 2.13–2.20 (m, 1H), 2.15 (s, 1H), 2.32–2.45(m, 1H), 2.87–3.05 (m, 2H), 4.42 (m, 1H), 4.75 (td, 1H), 5.24 (s, 2H), 5.25 (s, 2H), 7.29–7.60 (m, 10H), 7.63(s, 1H), 7.74(d, 1H), 8.37(s, 1H).

Step 2:
3-Hydroxymethyl-4-phenyl-7-[3-[4-(4-hydroxy-2-oxo)-tetrahydropyranyl]benzyloxy-2-naphthoic acid, sodium salt Following the procedure described in Example 1, Step 2, but substituting the lactone from Step 1 for 3-hydroxymethyl-4-phenyl-7-[3-[4-(4-methoxy)tetrahydropyranyl]benzyloxy]-2-naphthoic acid, lactone form, the title product is obtained.

What is claimed is:
1. A compound of the formula:

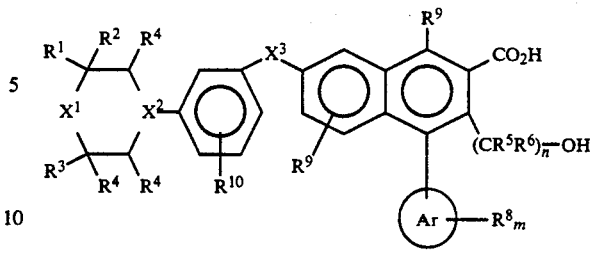

wherein:

$R^1$ and $R^5$ are independently H, OH, lower alkyl, or lower alkoxy;

$R^2$ is H, lower alkyl or together with $R^1$ forms a double bonded oxygen (=O);

$R^3$ is H, lower alkyl or together with $R^1$ forms a carbon bridge of 2 or 3 carbon atoms, said bridge optionally containing a double bond;

each $R^4$, $R^6$ and $R^7$ is independently H or lower alkyl;

$R^8$ is halogen, lower alkyl, or lower alkoxy;

each $R^9$ is independently H, halogen, lower alkyl, or lower alkoxy;

$R^{10}$ is H, halogen, lower alkyl, or lower alkoxy;

$X^1$ is O, S, S(O), $S(O)_2$, or $CH_2$;

$X^2$ is N, N(O), $C(OR^7)$, or $C(R^7)$;

$X^3$ is $CH_2O$, $OCH_2$, or $CH_2CH_2$;

Ar is phenyl or 1- or 2-naphthyl;

m is 0, 1, or 2;

n is 1 or 2;

or the pharmaceutically acceptable salts thereof.

2. A compound of claim 1 of the formula:

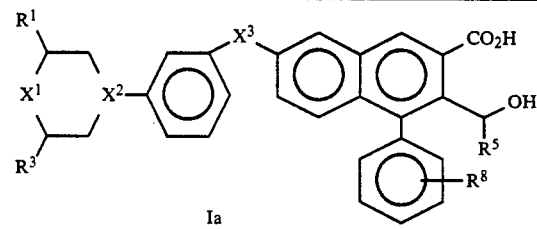

Ia wherein the substituents are:

| Ex. | $R^1$ | $R^3$ | $R^5$ | $R^8$ | $X^1$ | $X^2$ | $X^3$ |
|---|---|---|---|---|---|---|---|
| 1 | H | H | H | H | O | C(OMe) | $CH_2O$ |
| 2 | H | H | H | H | O | C(OMe) | $OCH_2$ |
| 3 | H | H | H | 4-F | O | C(OMe) | $CH_2O$ |
| 4 | H | H | H | H | O | C(OH) | $CH_2O$ |
| 5 | H | H | H | H | O | C(OEt) | $CH_2O$ |
| 6 | H | H | H | H | $CH_2$ | C(OMe) | $CH_2O$ |
| 7 | H | H | H | H | O | N | $CH_2O$ |
| 8 | H | H | H | H | O | N(O) | $CH_2O$ |
| 9 | H | H | OH | H | O | C(OMe) | $CH_2O$ |
| 10 | OH | H | H | H | O | C(OMe) | $CH_2O$ |
| 11 | OH | H | H | H | O | C(OH) | $CH_2O$ |
| 12 | H | H | OH | H | O | C(OH) | $CH_2O$ |
| 13 | OH | H | OH | H | O | C(OH) | $CH_2O$ |
| 14 | H | H | Me | H | O | C(OMe) | $CH_2O$ |
| 15 | OH | H | OH | H | O | C(OMe) | $CH_2O$ |
| 16* | Me | Me | H | H | O | C(OH) | $CH_2O$ |
| 17* | Me | Me | H | H | O | C(OH) | $CH_2O$ |
| 18 | H | H | H | 4-Cl | O | C(OH) | $CH_2O$ |
| 19 | H | H | H | 4-OMe | O | C(OH) | $CH_2O$ |
| 20 | Me | Me | H | H | O | C(OMe) | $CH_2O$ |
| 21 | H | H | H | H | S | C(OH) | $CH_2O$ |
| 22 | H | H | H | H | S(O) | C(OH) | $CH_2O$ |
| 23 | H | H | H | H | $S(O)_2$ | C(OH) | $CH_2O$ |
| 24** | OMe | H | H | H | O | C(OH) | $CH_2O$ |
| 25** | OMe | H | H | H | O | C(OH) | $CH_2O$ |
| 26 | H | H | H | H | O | C(Me) | $CH_2O$ |

-continued

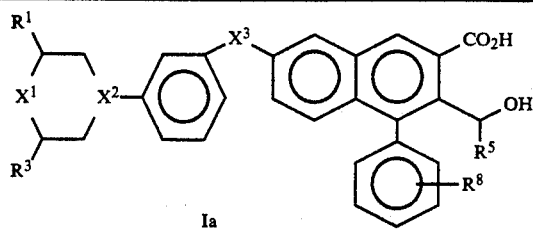

Ia wherein the substituents are:

| Ex. | R¹ | R³ | R⁵ | R⁸ | X¹ | X² | X³ |
|---|---|---|---|---|---|---|---|
| 27 | H | H | Me | H | O | C(OH) | CH₂O |
| 28 | H | H | H | 4-F | O | C(OH) | CH₂O |
| 29 | H | H | H | H | O | C(Et) | CH₂O |
| 30 | H | H | H | 2-F | O | C(OH) | CH₂O |
| 31 | H | H | H | 2-Cl | O | C(OH) | CH₂O |
| 32 | H | H | H | 3-OMe | O | C(OH) | CH₂O |
| 33** | OCH(Me)₂ | H | H | H | O | C(OH) | CH₂O |
| 34** | OCH(Me)₂ | H | H | H | O | C(OH) | CH₂O |
| 35 | (R¹R³)= | —CH=CH— | H | H | O | C(OH) | CH₂O |
| 36 | (R¹R³)— | —CH₂CH₂— | H | H | O | C(OH) | CH₂O |

*cis and trans isomers
**axial and equatorial isomers

3. A compound of claim 1 of formula:

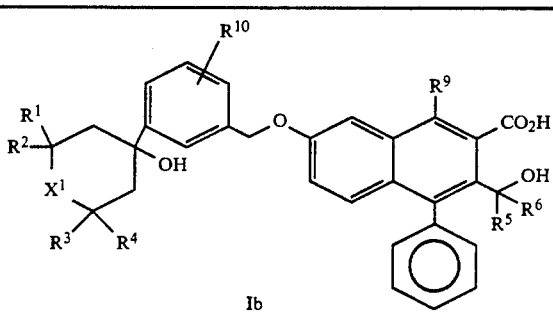

Ib wherein the substituents are:

| Ex. | R¹ | R² | R³ | R⁴ | R⁵ | R⁶ | R⁹ | R¹⁰ | X¹ |
|---|---|---|---|---|---|---|---|---|---|
| 37 | H | H | H | H | H | H | H | 4-Ome | O |
| 38 | H | H | H | H | Me | Me | H | H | O |
| 39 | H | H | H | H | H | H | 1-OMe | H | O |
| 40 | Me | Me | Me | Me | H | H | H | H | S |
| 41 | (R¹R²)= | =O | H | H | H | H | H | H | O |

4. A following compounds of claim 1:

3-Hydroxymethyl-4-phenyl-7-{3-[4-(4-methoxy)tetrahydropyranylbenzyloxy}-2-naphthoic acid, sodium salt;

3-Hydroxymethyl-4-phenyl-7-{3-[4-(4-methoxy)tetrahydropyranyl]phenoxymethyl}-2-naphthoic acid, sodium salt;

3-Hydroxymethyl-4-(4-fluorophenyl)-7-{3-[4-(4-methoxy)tetrahydropyranyl]benzyloxy}-2-naphthoic acid, sodium salt;

3-Hydroxymethyl-4-phenyl-7-{3-[4-(4-hydroxy)tetrahydropyranyl]benzyloxy}-2-naphthoic acid, sodium salt;

3-Hydroxymethyl-4-phenyl-7-{3-[4-(4-ethoxy)tetrahydropyranyl]benzyloxy}-2-naphthoic acid, sodium salt;

3-Hydroxymethyl-4-phenyl-7-{3-(1-methoxycyclohexyl)benzyloxy}-2-naphthoic acid, sodium salt;

3-Hydroxymethyl-4-phenyl-7-{3-(N-morpholino)benzyloxy}-2-naphthoic acid, sodium salt;

3-Hydroxymethyl-4-phenyl-7-{3-(N-oxomorpholino)benzyloxy}-2-naphthoic acid, sodium salt;

3-Formyl-4-phenyl-7-{3-[4-(4-methoxy)tetrahydropyranyl)benzyloxy}-2-naphthoic acid, sodium salt;

3-Hydroxymethyl-4-phenyl-7-[3-[4-(2,4-dihydroxy)tetrahydropyranyl]benzyloxy]-2-naphthoic acid, sodium salt;

3-Formyl-4-phenyl-7-[3-[4-(4-hydroxy)tetrahydropyranyl]benzyloxy]-2-naphthoic acid, sodium salt;

3-Hydroxymethyl-4-phenyl-7-[3-[4-(4α-hydroxy-2,6-dimethyl)tetrahydropyranyl]benzyloxy]-2-naphthoic acid, sodium salt;

3-Hydroxymethyl-4-phenyl-7-[3-[4-(4β-hydroxy-2,6-dimethyl)tettahydropyranyl]benzyloxy]-2-naphthoic acid, sodium salt;

3-Hydroxymethyl-4-(4-chlorophenyl)-7-[3-[4-(4-hydroxy)tetrahydropyranyl]benzyloxy]-2-naphthoic acid, sodium salt;

3-Hydroxymethyl-4-(4-methoxyphenyl)-7-[3-[4-hydroxy)tetrahydropyranyl]benzyloxy]-2-naphthoic acid, sodium salt;

3-Hydroxymethyl-4-phenyl-7-[3-[4-(4α-methoxy-2,6-dimethyl)tetrahydropyranyl]benzyloxy]-2-naphthoic acid, sodium salt;

3-Hydroxymethyl-4-phenyl-7-[3-[4-(4-hydroxy)tetrahydrothiopyranyl]benzyloxy]-2-naphthoic acid, sodium salt;

3-Hydroxymethyl-4-phenyl-7-[3-[4-(4-hydroxy-S-oxo)tetrahydrothiopyranyl]benzyloxy]-2-naphthoic acid, sodium salt;

3-Hydroxymethyl-4-phenyl-7-[3-[4-(4-hydroxy-S,S-dioxo)tetrahydrothiopyranyl]benzyloxy]-2-naphthoic acid, sodium salt;

3-Hydroxymethyl-4-phenyl-7-[3-[4-(4-hydroxy-2α-methoxytetrahydropyranyl]benzyloxy]-2-naphthoic acid, sodium salt;

3-Hydroxymethyl-4-phenyl-7-[3-[4-(4-hydroxy-2β-methoxytetrahydropyranyl]benzyloxy]-2-naphthoic acid, sodium salt;

3-Hydroxymethyl-4-phenyl-7-[3-[4-(4-methyl)tetrahydropyranyl]benzyloxy]-2-naphthoic acid, sodium salt;

3-(1-Hydroxyethyl)-[3-[4-hydroxy)tetrahydropyranyl]benzyloxy]-4-phenyl-2-naphthoic acid, sodium salt;

3-Hydroxymethyl-4-(4-fluorophenyl)-7-[3-[4-(4-hydroxy)tetrahydropyranyl]benzyloxy]-2-naphthoic acid, sodium salt;

3-Hydroxymethyl-4-phenyl-7-[3-[4-(4-ethyl)tetrahydropyranyl]benzyloxy]-2-naphthoic acid, sodium salt;

3-Hydroxymethyl-4-(fluorophenyl)-7-[3-[4-(4-hydroxy)tetrahydropyranyl]benzyloxy]-2-naphthoic acid, sodium salt;

3-Hydroxymethyl-4-(2-chlorophenyl)-7-[3-[4-(4-hydroxy)tetrahydropyranyl]benzyloxy]-2-naphthoic acid, sodium salt;

3-Hydroxymethyl-4-(3-methoxyphenyl)-7-[3-[4-(4-hydroxy)tetrahydropyranyl]benzyloxy]-2-naphthoic acid, sodium salt;

3-Hydroxymethyl-4-phenyl-7-[3-[4-(4-hydroxy-2α-isopropyloxy)tetrahydropyranyl]benzyloxy]-2-naphthoic acid, sodium salt;

3-Hydroxymethyl-4-phenyl-7-[3-[4-(4-hydroxy-2β-isopropyloxy)tetrahydropyranyl]benzyloxy]-2-naphthoic acid, sodium salt;

3-Hydroxymethyl-4-phenyl-7-[3-[3-(8-oxabicyclo[3,2,1]oct-6-en-3α-ol)]benzyloxy]-2-naphthoic acid, sodium salt;

3-Hydroxymethyl-4-phenyl-7-[3-[3-(8-oxabicyclo[3.2.1]octan-3α-ol)]benzyloxy]-2-naphthoic acid, sodium salt;

3-Hydroxymethyl-4-phenyl-7-[3-[4-(hydroxy)tetrahydropyranyl]-4-methoxybenzyloxy]-2-naphthoic acid, sodium salt;

3-(1-Hydroxy-1-methylethyl)-4-phenyl-7-[3-[4-(4-hydroxy)tetrahydropyranyl]benzyloxy]-1-naphthoic acid, sodium salt;

3-Hydroxymethyl-7-[3-[4-(4-hydroxy)tetrahydropyranyl]benzyloxy]-1-methoxy-4-phenyl-2-naphthoic acid, sodium salt;

3-Hydroxymethyl-4-phenyl-7-[3-[4-(4α-hydroxy-2,2,6,6-tetramethyl)tetrahydrothiopyranyl]benzyloxy]-2-naphthoic acid, sodium salt; or 3-Hydroxymethyl-4-phenyl-7-[3-[4-(4-hydroxy-2-oxo)tetrahydropyranyl]benzyloxy-2-naphthoic acid, sodium salt.

* * * * *